US00RE44812E

(19) United States
(12) Reissued Patent
Hedges

(10) Patent Number: US RE44,812 E
(45) Date of Reissued Patent: Mar. 18, 2014

(54) METHOD FOR EXTRACTING HYDROPHOBIN FROM A SOLUTION

(71) Applicant: Conopco, Inc., Englewood Cliffs, NJ (US)

(72) Inventor: Nicholas David Hedges, Sharnbrook (GB)

(73) Assignee: Conopco, Inc., Englewood Cliffs, NJ (US)

(21) Appl. No.: 13/954,091

(22) Filed: Jul. 30, 2013

Related U.S. Patent Documents

Reissue of:

(64) Patent No.: 8,354,503
Issued: Jan. 15, 2013
Appl. No.: 12/636,157
Filed: Dec. 11, 2009

(30) Foreign Application Priority Data

Dec. 16, 2008 (EP) ..... 08171868

(51) Int. Cl.
*C07K 1/14* (2006.01)
*A61K 31/731* (2006.01)
*A61K 38/00* (2006.01)

(52) U.S. Cl.
USPC ..... 530/344; 530/350; 530/361; 424/493; 424/499

(58) Field of Classification Search
CPC ..... A61K 31/731
See application file for complete search history.

(56) References Cited

U.S. PATENT DOCUMENTS

| | | | |
|---|---|---|---|
| 2,604,406 | A | 7/1952 | Blihovde |
| 2,844,470 | A | 7/1958 | Akerboom et al. |
| 2,937,093 | A | 5/1960 | Gorman et al. |
| 2,970,017 | A | 2/1961 | Melnick |
| 2,970,917 | A | 2/1961 | Melnick |
| 3,266,214 | A | 8/1966 | Kramme |
| 3,346,387 | A | 10/1967 | Moncrieff et al. |
| 3,914,441 | A | 10/1975 | Finney et al. |
| 3,946,122 | A | 3/1976 | Scharp |
| 4,066,794 | A | 1/1978 | Schur |
| 4,146,652 | A | 3/1979 | Kahn et al. |
| 4,305,964 | A | 12/1981 | Moran et al. |
| 4,325,980 | A | 4/1982 | Rek et al. |
| 4,425,369 | A | 1/1984 | Sakamoto et al. |
| 4,542,035 | A | 9/1985 | Huang et al. |
| 4,627,631 | A | 12/1986 | Sherman |
| 4,627,983 | A | 12/1986 | Scharf et al. |
| 4,629,628 | A | 12/1986 | Negro |
| 4,668,519 | A | 5/1987 | Dartey et al. |
| 4,869,915 | A | 9/1989 | Inayoshi et al. |
| 4,874,627 | A | 10/1989 | Greig et al. |
| 4,946,625 | A | 8/1990 | O'Lenick |
| 4,954,440 | A | 9/1990 | Johal et al. |
| 4,960,540 | A | 10/1990 | Friel et al. |
| 5,084,295 | A | 1/1992 | Whelan et al. |
| 5,104,674 | A | 4/1992 | Chen et al. |
| 5,202,147 | A | 4/1993 | Traska et al. |
| 5,208,028 | A | 5/1993 | Clement et al. |
| 5,215,777 | A | 6/1993 | Asher et al. |
| 5,336,514 | A | 8/1994 | Jones et al. |
| 5,393,549 | A | 2/1995 | Badertscher et al. |
| 5,397,592 | A | 3/1995 | Vermaas et al. |
| 5,436,021 | A | 7/1995 | Bodor et al. |
| 5,486,372 | A | 1/1996 | Martin et al. |
| 5,536,514 | A | 7/1996 | Bishay et al. |
| 5,620,732 | A | 4/1997 | Clemmings et al. |
| 5,624,612 | A | 4/1997 | Sewall et al. |
| 5,681,505 | A | 10/1997 | Phillips et al. |
| 5,738,897 | A | 4/1998 | Gidley |
| 5,770,248 | A | 6/1998 | Liebfred et al. |
| 5,980,969 | A | 11/1999 | Mordini et al. |
| 6,063,602 | A | 5/2000 | Prosperi et al. |
| 6,096,867 | A | 8/2000 | Byass et al. |
| 6,187,365 | B1 | 2/2001 | Vaghela et al. |
| 6,238,714 | B1 | 5/2001 | Binder et al. |
| 6,284,303 | B1 | 9/2001 | Rowe et al. |
| 6,497,913 | B1 | 12/2002 | Gray et al. |
| 6,579,557 | B1 | 6/2003 | Benjamins et al. |
| 6,685,977 | B1 | 2/2004 | Asano et al. |
| 6,914,043 | B1 | 7/2005 | Chapman et al. |
| 7,338,779 | B1 | 3/2008 | Nakari-Setala et al. |
| 8,178,151 | B2 | 5/2012 | Bramley et al. |
| 8,206,770 | B2 | 6/2012 | Aldred et al. |
| 8,216,624 | B2 | 7/2012 | Berry et al. |
| 8,354,503 | B2 | 1/2013 | Hedges et al. |
| 8,357,420 | B2 | 1/2013 | Cox et al. |

(Continued)

FOREIGN PATENT DOCUMENTS

| | | | |
|---|---|---|---|
| CA | 271999 | A | 6/1927 |
| CA | 1094866 | | 10/2003 |

(Continued)

OTHER PUBLICATIONS

Jan. 1, 2005, Fats Oils Fatty Acids Triglycerides, Scientific Psychic, 1-4.

Jun. 14, 2010, Guar Gum, Guargum.biz, 1.

Oct. 16, 2009, Search proteins matching the sequence pattern used for the hydrophobin definition in patent EP 1926 399 B1, Nestle Research Center, 1-3.

Arbuckle, Jan. 1, 1972, Ice Cream, Ice Cream 2nd Ed, pp. 15, 18, 31, 35, 61, 65, 265-266 and 284-285.

Askolin, et al., Aug. 9, 2001, Overproduction purification and characterization of *Trichoderma reesei* hydrophobin HFBI, Appl Microbiol Biotechnol, 57, 124-130.

Askolin, et al., Jan. 10, 2006, Interaction & comparison of a Class I Hydrophobin from schizophyllum commune & Class II Hydro form *trichoderma reesei*, Biomacromolecules, 7, 1295-1301.

Bailey, et al., Jan. 31, 2002, Process Technol effects of deletion & amplification of hydrophobins I & II in transformants of *Trich reesei*, Appl Microbiol Biotechnol, 58, 721-727.

Bay, Jan. 1, 2002, La Cucina Italiana Italian Cuisine, Edizioni Piemme, *, 1233.

(Continued)

*Primary Examiner* — Manjunath Rao
*Assistant Examiner* — Samuel Liu
(74) *Attorney, Agent, or Firm* — Alan A. Bornstein

(57) ABSTRACT

Process for extracting hydrophobin from a solution wherein carrageenan is added to the solution and the pH of the solution is brought below 3.5, and the ionic strength of the solution is below 0.5.

22 Claims, No Drawings

(56) References Cited

U.S. PATENT DOCUMENTS

| | | | |
|---|---|---|---|
| 8,394,444 | B2 | 3/2013 | Cox et al. |
| 2001/0048962 | A1 | 12/2001 | Fenn et al. |
| 2002/0085987 | A1* | 7/2002 | Brown et al. ..... 424/70.11 |
| 2002/0155208 | A1 | 10/2002 | Benjamins et al. |
| 2002/0182300 | A1 | 12/2002 | Groh et al. |
| 2002/0197375 | A1 | 12/2002 | Adolphi et al. |
| 2003/0087017 | A1 | 5/2003 | Hanselmann et al. |
| 2003/0099751 | A1 | 5/2003 | Aldred et al. |
| 2003/0134025 | A1 | 7/2003 | Vaghela et al. |
| 2003/0148400 | A1 | 8/2003 | Haikara et al. |
| 2003/0166960 | A1 | 9/2003 | de Vocht et al. |
| 2003/0175407 | A1 | 9/2003 | Kunst et al. |
| 2003/0190402 | A1 | 10/2003 | McBride |
| 2004/0109930 | A1 | 6/2004 | Hooft et al. |
| 2004/0161503 | A1 | 8/2004 | Malone et al. |
| 2004/0185162 | A1 | 9/2004 | Finnigan et al. |
| 2005/0037110 | A1 | 2/2005 | Windhab et al. |
| 2005/0058058 | A1 | 3/2005 | Cho et al. |
| 2005/0123666 | A1 | 6/2005 | Vaghela et al. |
| 2005/0123668 | A1 | 6/2005 | Kodali et al. |
| 2005/0129810 | A1 | 6/2005 | Lindner et al. |
| 2005/0193744 | A1 | 9/2005 | Cockings et al. |
| 2006/0024417 | A1 | 2/2006 | Berry et al. |
| 2006/0024419 | A1 | 2/2006 | Aldred et al. |
| 2007/0014908 | A1 | 1/2007 | Bramley et al. |
| 2007/0071865 | A1 | 3/2007 | Aldred et al. |
| 2007/0071866 | A1 | 3/2007 | Cox et al. |
| 2007/0116848 | A1 | 5/2007 | Aldred et al. |
| 2007/0286936 | A1 | 12/2007 | Bramley et al. |
| 2007/0298490 | A1 | 12/2007 | Sweigard et al. |
| 2008/0175972 | A1 | 7/2008 | Cox |
| 2008/0254180 | A1 | 10/2008 | Windhab et al. |
| 2008/0305237 | A1 | 12/2008 | Beltman et al. |
| 2009/0136433 | A1 | 5/2009 | Subkowski et al. |
| 2009/0142467 | A1 | 6/2009 | Aldred et al. |
| 2010/0303998 | A1 | 12/2010 | Cox et al. |

FOREIGN PATENT DOCUMENTS

| | | | |
|---|---|---|---|
| CA | 1218557 | | 11/2004 |
| CN | 101054407 | | 10/2007 |
| CN | 101215321 | | 7/2008 |
| DE | 29715519 | | 11/1997 |
| DE | 102004038685 | | 2/2006 |
| EP | 216270 | | 4/1987 |
| EP | 0274348 | | 7/1988 |
| EP | 0285198 | | 10/1988 |
| EP | 0322952 | A2 | 7/1989 |
| EP | 0336817 | | 10/1989 |
| EP | 0426211 | | 5/1991 |
| EP | 0426211 | A1 | 5/1991 |
| EP | 0469656 | | 2/1992 |
| EP | 0521543 | | 1/1993 |
| EP | 0477825 | B1 | 12/1996 |
| EP | 775444 | A1 | 5/1997 |
| EP | 0777969 | | 6/1997 |
| EP | 0777969 | B1 | 6/1997 |
| EP | 0930017 | | 7/1999 |
| EP | 0930017 | A1 | 7/1999 |
| EP | 1061006 | | 12/2000 |
| EP | 1074181 | A1 | 2/2001 |
| EP | 0747301 | | 8/2001 |
| EP | 0783254 | B1 | 8/2001 |
| EP | 0919134 | | 11/2001 |
| EP | 0771531 | B1 | 9/2002 |
| EP | 1284106 | | 2/2003 |
| EP | 0995685 | | 4/2003 |
| EP | 1400486 | | 3/2004 |
| EP | 1520483 | | 4/2005 |
| EP | 1520484 | | 4/2005 |
| EP | 1520485 | | 4/2005 |
| EP | 1557092 | | 7/2005 |
| EP | 1621084 | | 2/2006 |
| EP | 1621084 | A1 | 2/2006 |
| EP | 1623631 | | 2/2006 |
| EP | 1626361 | A1 | 2/2006 |
| EP | 1541034 | A1 | 6/2006 |
| EP | 1849461 | A1 | 10/2007 |
| EP | 2052628 | | 4/2009 |
| EP | 2052628 | A1 | 4/2009 |
| GB | 459583 | | 1/1937 |
| GB | 1556297 | | 11/1979 |
| JP | 530006491 | | 1/1978 |
| JP | 530006491 | | 7/1978 |
| JP | 61219342 | | 9/1986 |
| JP | 61293348 | | 12/1986 |
| JP | 03164156 | | 7/1991 |
| JP | 3244348 | A | 10/1991 |
| JP | 08500486 | | 1/1996 |
| JP | 2005278484 | | 10/2005 |
| KR | 2004018844 | | 3/2004 |
| WO | WO9013571 | | 11/1990 |
| WO | WO9111109 | | 8/1991 |
| WO | WO9222581 | | 12/1992 |
| WO | WO9403617 | | 2/1994 |
| WO | WO9412050 | | 6/1994 |
| WO | WO9413154 | | 6/1994 |
| WO | WO9523843 | | 9/1995 |
| WO | WO9611586 | | 4/1996 |
| WO | WO9621362 | | 7/1996 |
| WO | WO9639878 | | 12/1996 |
| WO | WO9641882 | | 12/1996 |
| WO | WO9804148 | | 2/1998 |
| WO | WO9804699 | | 2/1998 |
| WO | WO9937673 | | 7/1999 |
| WO | WO9954725 | | 10/1999 |
| WO | WO0022936 | | 4/2000 |
| WO | WO0053026 | | 9/2000 |
| WO | WO0058342 | | 10/2000 |
| WO | WO0114521 | | 3/2001 |
| WO | WO0135756 | A1 | 5/2001 |
| WO | WO0157076 | | 8/2001 |
| WO | WO0174864 | | 10/2001 |
| WO | WO0183534 | | 11/2001 |
| WO | WO0184945 | A1 | 11/2001 |
| WO | WO03015530 | A1 | 2/2003 |
| WO | WO03051136 | A1 | 6/2003 |
| WO | WO03053383 | A2 | 7/2003 |
| WO | WO03053883 | | 7/2003 |
| WO | WO03096821 | | 11/2003 |
| WO | WO2005058055 | | 6/2005 |
| WO | WO2005058067 | A1 | 6/2005 |
| WO | WO2005102067 | | 11/2005 |
| WO | WO2005113387 | | 12/2005 |
| WO | WO2005113387 | A2 | 12/2005 |
| WO | WO2006010425 | | 2/2006 |
| WO | WO2007087967 | | 8/2007 |
| WO | WO2008031796 | A1 | 3/2008 |
| WO | WO2008116733 | | 10/2008 |
| WO | WO2009047657 | A2 | 4/2009 |
| WO | WO2010067059 | | 6/2010 |
| WO | WO2010067059 | A1 | 6/2010 |

OTHER PUBLICATIONS

Berolzheimer, Jan. 1, 1988, Culinary Arts Institute Encyclopedic Cookbook, Culinart Arts Institute, *, 648.

Calonje, et al., Dec. 13, 2002, Properties of a hydrophobin isolated from the mycoparasitic fungus *verticillium fungicola*, Can J Microbiol, 48, 1030-1034.

Chaisalee, et al., Oct. 1, 2003, Mechanism of Antifoam Behavior of Solutions of Nonionic Surfactants Above the Cloud Point, Journal of Surfactants & Detergents, 6, No. 4, 345-351.

Chakraborty, et al., Jan. 1, 1972, Stabilization of Calcium Sensitive Plant Proteins by k-Carrageenan, Journal of Food Science, 37, 719-721.

Cheer, et al., Jan. 1, 1983, Effects of Sucrose on the Rheological Behavior of Wheat Starch Pastes, Journal of Applied Polymer Science, 28, 1829-1836.

Collen, et al., Jan. 15, 2002, A novel two-step extraction method w detergent polymer sys for primary recovery of the fusion protein endoglucanase I-hydro I, Biochimica et Biophysica Acta, 1569, No. 1-3, 139-150.

(56) References Cited

OTHER PUBLICATIONS

CP Kelco US Inc., Apr. 17, 2007, Certificate of Analysis for Keltrol RD, CP Kelco, *, 1.
CRC Jan. 1, 2008, Fennema's Food Chemistry, CRC Press, 4th Ed., pp. 727-728, Taylor & Francis Group.
Cruse, May 26, 1970, Whipped Soup is Tasty, St. Petersberg Independant, ., B-4, p. 1.
Damodaran, Oct. 27, 2004, Adsorbed layers formed from mixtures of proteins, Current Opinion to Colloid & Interface Science, 9, 328-339.
Davis, et al., Jan. 1, 2001, Application of foaming for the recovery of surfactin from *B. subtilis* ATCC 21332 cultures, Enzyme & Microbial Technology, 28, 346-354.
De Vocht et al., Apr. 1998, Structural Characterization of the Hydrophobin SC3, as a Monomer and after Self-Assembly at Hydrophobic/Hydrophilic Interfaces, Biophysical Journal, 74, 2059-2068.
De Vries, et al., Mar. 2, 1999, Identification & characterization of a tri-partite hydrophobin from *Claviceps fusiformis*, Eur J Biochem, 262, 377-385.
Dictionary.com, Jun. 14, 2010, Stabilizer, Dictionary.com, *, 1-5.
Dr. E. Kododziejcxzyk, Nov. 16, 2009, Adsortion of different proteins to Teflon sheets: Experimental Results, Nestle Research Center, pp. 1-10.
Fellows, 2000, Principles and Practice, Food processing technology, 2nd, 83, 140, 429, Foodhead Publishing.
Goh, Apr. 8, 2002, Applications and Uses of Palm and Palm Kernel Oils, Malaysian Oil Science and Technology, 11, 46-50.
Grant, Jan. 1, 1987, Grant & Hackh's Chemical Dictionary, McGraw-Hill, 5th Ed, 212.
Guner, et al., Jan. 1, 2007, Production of yogurt ice cream at different acidity, Intl Journ of Food Sc & Tech, 42, 948-952.
Hakanpaa, et al., Jan. 2, 2004, Atomic Resolution Structure of the HFBII Hydrophobin a Self-assembling Amphiphile, Journal of Biological Chemistry, 279, No. 1, 534-539.
Holmes, et al., Oct. 10, 2006, Evaluation of antifoams in the expression of a recombinant FC fusion protein in shake flask cultures, Microbial Cell Factories, 5, No. 1, pp. 1-3.
Hung, et al., Aug. 20, 2007, Cloud-point extraction of selected polycyclic aromatic hydrocarbons by nonionic surfactants, Separation & Purification Tech, 57, 1-10.
Hunter, et al., Jan. 1, 2008, The role of particles in stabilising foams and emulsions, Advances in Colloid & Interface Science, 137, 57-81.
Katzbauer et al, Jun. 19, 1997, Properties and applications of xanthan gum, Polymer Degradation and Stability, vol. 59, 81-84, Elsevier.
Kershaw, et al., Jan. 1, 1998, Hydrophobins and Repellents Proteins with Fundamental Roles in Fungal Morphogenesis, Genetics & Biology, 23, 18-33.
Kilcast et al., Jun. 20, 2002, Sensory perception of creaminess and its relationship with food structure, Food Quality and Preference, 13, 609-623.
Kloek, et al., Feb. 2, 2001, Effect of Bulk and Interfacial Rheological Properties on Bubble Dissolution, Journal of Colloid & Interface Sc, 237, 158-166.
Lambou et al., 1973, Whey Solids as Agricultural Foam Stabilizers, Jr. of Agr. and Food Chemistry, 21 No. 2, 257-263.
Linder, Jan. 21, 2005, Hydrophobins: the protein-amphiphiles of filamentous fungi, Microbiology Reviews, vol. 29 No. 5, 877-896.
Linder, et al., Jul. 1, 2001, The hydrophobins HFBI & HFBII from *Trichoderma reesei* showing efficient interatctions w nonionic surfactants in aqueous two-phase sys, Biomacromolecules, 2, No. 2, 511, 514, 515, 516.
Lumsdon, et al., Sep. 1, 2005, Adsorption of hydrophobin proteins at hydrophobic & hydrophilic interfaces, Colloids & Surfaces, 44, 172-178.
Marshall, Jan. 1, 2003, Ice Cream, Springer, 6th Ed, 70-73.
Martin, et al., Jan. 14, 2000, Sc30 Hydrophobin Organization in Aqueous Media & Assembly onto Surfaces as Mediated by Assoc Polysaccharide Schizophyllan, Biomacromolecules, 1, 49-58.
Mathlouthi, et al., Jan. 1, 1995, Rheological properties of sucrose solutions and suspensions, Sucrose Properties & Applic, *, 126-154.
McCabe, et al., Dec. 1, 1999, Secretion of Cryparin a Fungal Hydrophobin, Applied & Environmental Microbiology, 65, No. 12, 5431-5435.
McGregor, et al., Jan. 1, 1988, Antifoam effects on ultrafiltration, Biotechnology & Bioengineering, 31, No. 4, 385-389.
Minor, et al., Jan. 1, 2009, Preparation and sensory perception of fat-free foams effect of matrix properties and level of aeration, Intl Journ of Food Sc & Tech, 44, 735-747.
Murray, Aug. 3, 2007, Stabilization of bubbles and foams, Current Opinion in Colloid & Interface Science, 12, 232-241.
Wang et al, Protease A Stability of Beer Foam II, China Academic Journal, May 31, 2004, pp. 11-15, ., CN.
Research pushes the right buttons, mushrooms are the new fat, University of Birmingham, Feb. 25, 2008, pp. 1-2.
Cox, et al., Jan. 1, 2009, Exceptional Stability of food foams using class II hydrophobin HFBII, Food Hydrocolloids, 23, 366-376.
Cox, et al., Jun. 20, 2007, Surface Properties of Class II Hydrophobins from *Trichoderma reesei* & Influence on bubble stability, Langmuir, 23, 7995-8002.
Pardun, 1977, Soy Protein Preparations as Antispattering Agents for Margarine, Fette Seifen Anstrichmittel, vol. 79, No. 5, pp. 195-203 (Abstract Only).
Samsudin, 2010, Low-Fat Chocolate Spread Based on Palm Oil, retrieved from Internet: http://palmoils.mpob.gov.my/pulibcations/pod45-salmi.pdf, pp. 27-30.
Kinderlerer, 1997, *Chrysosporium* species, potential spoilage organisms of chocolate, Jr. of Applied Microbiology, vol. 83, pp. 771-778.
Scott et al., 1983, Influence of Temperature on the Measurement of Water Activity of Food and Salt Systems, Journal of Food Science, vol. 48, pp. 552-554.
Co-Pending application Aldred et al., U.S. Appl. No. 11/525,060, filed Sep. 21, 2006; pp. 1-32.
Co-Pending application Aldred et al., U.S. Appl. No. 11/524,977, filed Sep. 21, 2006; pp. 1-39.
Co-pending application Cox et al., U.S. Appl. No. 11/524,675, filed Sep. 21, 2006, pp. 1-19.
Co-Pending application Cox et al., U.S. Appl. No. 11/699,601, filed Jan. 30, 2007, pp. 1-28.
Co-Pending application Cox et al., U.S. Appl. No. 11/699,602, filed Jan. 30, 2007, pp. 1-26.
Co-Pending application Burmester et al., U.S. Appl. No. 12/002,684, filed Dec. 18, 2007, pp. 1-35.
Co-Pending application Burmester et al., U.S. Appl. No. 13/091,796, filed Apr. 21, 2011, pp. 1-35.
Co-Pending application Cox et al., U.S. Appl. No. 12/682,717, filed Apr. 12, 2010; pp. 1-27.
Co-Pending application Aldred et al., U.S. Appl. No. 12/287,957, filed Oct. 15, 2008; pp. 1-28.
Co-Pending application Cox et al., U.S. Appl. No. 12/578,752, filed Oct. 14, 2009; pp. 1-14.
Co-Pending application Aldred et al., U.S. Appl. No. 12/788,395, filed May 27, 2010; pp. 1-13.
Co-Pending application Watts et al., U.S. Appl. No. 12/788,419, filed May 27, 2010; pp. 1-15.
Co-Pending application Cox et al., U.S. Appl. No. 12/532,667, filed Sep. 23, 2009; pp. 1-18.
Co-Pending application Cox et al., U.S. Appl. No. 12/532,670, filed Sep. 23, 2009; pp. 1-23.
Co-Pending application Aldred et al., U.S. Appl. No. 13/378,143, filed Feb. 10, 2012; pp. 1-15.
Co-Pending application Mitchell et al., U.S. Appl. No. 13/498,157, filed Mar. 26, 2012; pp. 1-16.
Co-Pending application Deborah Lynne Aldred et al., U.S. Appl. No. 13/992,299, filed Jun. 7, 2013, pp. 1-11.
Co-Pending application Deborah Lynne Aldred et al., U.S. Appl. No. 13/989,820, filed Jun. 21, 2013, pp. 1-11.
Co-Pending application Deborah Lynne Aldred et al., U.S. Appl. No. 13/982,292, filed Jul. 29, 2013.
Co-Pending application Andrew Richard Cox et al., U.S. Appl. No. 13/585,257, filed Aug. 14, 2012, pp. 1-32.
Co-Pending application Aumaitre et al., U.S. Appl. No. 12/409,549, filed Mar. 24, 2009; pp. 1-19.

(56) References Cited

OTHER PUBLICATIONS

Co-Pending application Cox, U.S. Appl. No. 13/878,491, filed Apr. 9, 2013; pp. 1-20.
Askolin, S., Characterization of the Trichoderma resel hydrophobins HFBI and HFBII, VTT Publication 601, May 2006, 1-99 ; I1-I19; VI1-V120.
Notice of Opposition and Grounds of Opposition, dated Dec. 23, 2009—Nestec S.A./Unilever N.V. (EP1926399).
Response to Notice of Opposition, dated Oct. 29, 2010—Nestec S.A./Unilever N.V. (EP1926399).
Talbot et al. (1996) MPG1 Encodes a Fungal Hydrophobin Involved in Surface Interactions during Infection-Related Development of Magnaporthe grisea, Plant Cell., vol. 8, No. 6, pp. 985-999.*
Martin et al. (2000) Sc3p hydrophobin organization in aqueous media and assembly onto surfaces as mediated by the associated polysaccharide schizophyllan, Biomacromol., vol. 1, No. 1, pp. 49-60.*
Linder et al. (2005) Hydrophobins: the protein-amphiphiles of filamentous fungi, FEMS Microbiol. Rev., vol. 29, No. 5, pp. 877-896.*
Reference (2012, updated), "Carbohydrates", pp. 1-29.*
Wosten, et al., Interfacial self-assmbly of a hydrophobin into an amphipathic protein membrane mediates fungal attachment to hydrophobic surfaces, EMBO Journal, Jan. 1, 1994, 13, 5848-5854.
Swern, Baileys Industrial Oil and Fat Products, John Wiley & Sons, Jan. 1, 1979, 1, 369.
Scholtmeijer, et al., Fungal hydrophobins in medical and technical applications, Appl Microbiol Biotechnol, May 19, 2001, 56, 1-8.
Arbuckle, Ice Cream, Avi Publishing, Jan. 1, 1972, 2nd Ed, 284.
Wosten, et al., Hydrophobins the fungal coat unravelled, Biophysica Acta, May 29, 2000, 1469, 79-86.
Talbot, Aerial Morphogenesis Enter the Chaplins, Current Biology, Sep. 16, 2003, 13, R696-R698.
Murray, et al., Foam stability proteins and nanoparticles, Current Opinion in Colloid & Interface Sc, Jan. 1, 2004, 9, 314-320.
Eleves, Teadora Gliga, Eleves, Jun. 8, 2007, &, 1.
Nakari-Setala, et al., Differential expression of the vegetative and spore-bound hydrophobins of Trichoderma reesei, Eur J. Biochem, May 26, 1997, 248, 415-423.
Tchuenbou-Magaia, et al., Hydrophobris stabilised air-filled emulsions for the food industry, Food Hydrocolloids, Mar. 16, 2009; 23, 1877-1885.
Hoi, Encyclopedia of Food Science & Technology, John Wiley & Sons, Jan. 1, 1992, 1, 204-210.
Wessels, Hydrophobins Proteins that Change the Nature of the Fungal Surface, Advances in Microbial Physiology, Jan. 1, 1997, 38, No. 38, 1-45.
Wosten, Hydrophobins Multipurpose Proteins, Annu Rev Microbiol, Jan. 1, 2001, 55, 625-646.
Co-pending appln. Berry et al., U.S. appl. No. 11/168,209, filed Jun. 27, 2005.
Co-pending appln. Aldred et al., U.S. Appl. No. 11/168,214, filed Jun. 27, 2005.
Co-pending appln. Bramley et al., U.S. Appl. No. 11/639,851, filed Dec. 15, 2006.
Co-pending appln. Cox et al., U.S. Appl. No. 12/780,294, filed May 14, 2010.
Co-pending appln. Cox et al., U.S. Appl. No. 12/780,323, filed May 14, 2010.
Dickinson, Dec. 2, 2010, Mixed biopolymers at interfaces: Competive adsorption and multilayer structures, Food Hydrocolloids, 25, 1966-1983.
Fox, 1992, Analytical methods for Milk Proteins, Advanced Dairy Chemistry 1: Proteins, vol. 1, pp. 1, 6-7.
Graham et al., Jul. 3, 1979, Proteins at Liquid Interfaces, Journal of Colloid and Interface Science, 70, 415-426.
Miquelim et al., 2010, pH Influence on the stability of foams with protein-polysaccharide complexes at their interfaces, Food Hydrocolloids, 24, No. 4, 398-405.
Patino and Pilosof, 2011, Protein-polysaccharide interactions at fluid interfaces, Food Hydrocolloids, 25, 1925-1937.
Schmitt, Feb. 27, 2012, Declaration of Christophe Schmitt, Declaration of Christophe Schmitt, 1-4.
Guinee et al., 2004, Salt in Cheese: Physical, Chemical and Biological Aspects, vol. 1, 3rd Ed., pp. 207-259.
Guar Gum, Guargum biz, Jun. 14, 2010, p. 1.
Penttila, et al., Molecular Biology of Trichoderma & Biotechnological Applications, Handbook of Fungal Biotech, Jan. 1, 2004, 2nd Ed. pp. 413-427.
Talbot, 7 Fungal Hydrophobins, Howard & Gow, Jan. 1, 2001, vol. 7, pp. 145-159.
Soukoulis, et al., Impact of the acidification process hydrocolloids & protein fortifiers on the physical & Sensory properties of frozen yogurt, Intl Journal of Dairy Tech, May 2, 2008, vol. 61, No. 2, pp. 170-177.
Whitcomb, et al., Rheology of Guar Solutions, Journal of Applied Polymer Sc, Jan. 1, 1980, vol. 25, pp. 2815-2827.
Quintas, et al., Rheology of superstaurated sucrose solutions, Journal of Food Engineering, Jan. 1, 2006, vol. 77, pp. 844-852.
Van Der Werf, Green coatings healthy foods and drug targeting, Leads in Life Science, Jan. 1, 2000, vol. 5, p. 1.
Russo, et al., Surface activity of the phytotoxin cerato-ulmin, Natl Research Council of Canada, Jan. 1, 1982, vol. 60, pp. 1414-1422.
Search proteins matching the sequence pattern used for the hydrophobin definition in patent EP 1926 399 B1, Nestle Research Center, Oct. 16, 2009, pp. 1-3.
Takai, et al., Cerato-ulmin, a wilting losin of ceratocystis ulmi: isolation & some properties of cerato-ulmin from the culture of C. ulmi, Phytopath, Jan. 1, 1978, vol. 91, pp. 129-146.
Wosten, et al., Interfacial self-assembly of a fungal hydrophobin to a hydrophobic rodlet layer, Plant Cell, Nov. 1, 1993, vol. 5, pp. 1567-1574.
Stringer, et al., Cerato-ulmin a toxin involved in dutch elm disease is a fungal hydrophobin, Plant Cell, Feb. 1, 1993, *, pp. 145-146.
Fats Oils Fatty Acids Triglycerides, Scientific Psychic, Jan. 1, 2005, pp. 1-4.
Wessels, et al., Fungal hydrophobins proteins that function at an interface, Trends in Plant Science, Jan. 1, 1996, vol. 1, No. 1, pp. 9-15.
Sienkiewicz, Whey and Whey Utiliztion, Verlag Th Mann, Jan. 1, 1990, 2nd Ed, pp. 82-33.
Arbuckle, Ice Cream, Ice Cream 2nd Ed 1972 pp. 35 266 284-285, Jan. 1, 1972, 2nd Edition, pp. 35, 266, 284-285.
Arbuckle, Ice Cream, Ice Cream, 1972, 2nd, p. 31.
Arbuckle, Ice Cream, Ice Cream, 1972, 2nd Ed., p. 265, Avi Publishing Company.
Sanderson, Applications of Xanthan Gum, British Polymer Jr., 1981, vol. 13, pp. 71-75.
Temple, Biological Roles for cerato-Ulmin, a Hydrophobin secreted by the elm pathogens, Opthiostoma ulmi and O. novo-ulmi, Micological Society of America, 2000, vol. 92, pp. 1-9.
European Search Report Application No. EP 08171868, dated May 18, 2009.
International Search Report, International Application No. PCT/EP2009/066258, mailed Mar. 4, 2010.
Written Opinion, International Application No. PCT/EP2009/066258.
Arbuckle, 1972, Ice Cream, Ice Cream, 2nd Edition, pp. 15, 18, 35, 61, 65.
Co-Pending application Hedges et al., U.S. Appl. No. 12/636,157, filed Dec. 11, 2009.
Fox, et al., Jan. 1, 2004, Cheese: Physical, Chemical and Biological Aspects, Cheese Chemistry, Physics & Microbiology, 3rd, vol. 1, 207-223 9 (Best Available Copy).

* cited by examiner

METHOD FOR EXTRACTING HYDROPHOBIN FROM A SOLUTION

Matter enclosed in heavy brackets [ ] appears in the original patent but forms no part of this reissue specification; matter printed in italics indicates the additions made by reissue.

*PRIORITY TO RELATED APPLICATIONS*

*This application is a reissue of U.S. Pat. No. 8,354,503 B2, which was filed Dec. 11, 2009, and was assigned U.S. application Ser. No. 12/636,157, which claims the benefit of European Application No. 08171868.6, filed Dec. 16, 2009. The entire contents of the above-identified applications are hereby incorporated by reference.*

TECHNICAL FIELD OF THE INVENTION

The present invention relates to method for extracting hydrophobin from a solution. In particular it relates to a method for extracting hydrophobin in a fermentation process.

BACKGROUND TO THE INVENTION

Foaming is a common problem in aerobic, submerged fermentations. Foaming is caused by the sparging of gas into the fermentation medium for the purpose of providing oxygen for the growth of the aerobic organism being cultivated (e.g. bacteria, yeasts, fungi, algae, cell cultures). If the fermentation medium contains surface active components such as proteins, polysaccharides or fatty acids, then foam can be formed on the surface of the medium as the sparged gas bubbles disengage from the liquid. Foaming creates a number of problems including the undesirable stripping of product, nutrients, and cells into the foam, and can make process containment difficult. A known method for controlling foaming is to use antifoams, of which several types are commonly used: silicone-based (e.g. polydimethylsiloxanes), polyalkylene glycols (e.g. polypropylene glycol), fatty acids, polyesters and natural oils (e.g. linseed oil, soybean oil). Antifoams replace foam-forming components on bubble surfaces, resulting in destruction of the foam by bubble coalescence. Antifoams are added at the start of and/or during the fermentation.

When the fermentation product is intended for use in foods, personal products or medicine, it is highly desirable that the product is excreted by the producing organism into the fermentation medium (i.e. extra-cellular, rather than intra-cellular production). This avoids the need to disrupt the cells by physical or chemical means in order to release the product for recovery. By maintaining the cells intact, the cellular material can be easily separated from the product so that it is free of intracellular and genetic material which is usually regarded as an undesirable contaminant. This can be especially important when the producing organism has been genetically modified. However, extra-cellular production may intensify the degree of foaming in the fermenter, especially if the product facilitates foam formation or enhances foam stability, for example a biosurfactant or a hydrophobin. The use of antifoams presents a particular problem in the extra-cellular production of such foaming agents for two reasons: firstly the amount of antifoam required is increased because the foaming agent itself contributes to foaming in the fermenter. Secondly, it is not necessary to remove the antifoam from most fermentation products since it is present in low concentrations which do not affect the functionality of the product. However, when the fermentation product is a foaming agent, the antifoam must be substantially removed since the presence of antifoam in the product will impair its functionality.

Bailey et al, Appl. Microbiol. Biotechnol. 58 (2002) pp 721-727 disclose the production of hydrophobins HFB I and HFB II by the fermentation of transformants of Trichoderma reesei. An antifoam (Struktol J633) was used to prevent foaming and the hydrophobin was purified using aqueous two phase extraction. However separation methods such as aqueous two phase extraction or chromatographic processes are expensive and may require food-incompatible chemicals.

It has now been found that, rather than removing the antifoam from the solution it is possible to remove the hydrophobin.

TESTS AND DEFINITIONS

Hydrophobins

Hydrophobins can be obtained by culturing filamentous fungi such as hyphomycetes (e.g. Trichoderma), basidiomycetes and ascomycetes. Particularly preferred hosts are food grade organisms, such as Cryphonectria parasitica which secretes a hydrophobin termed cryparin (MacCabe and Van Alfen, 1999, App. Environ. Microbiol 65: 5431-5435). Similarly, surfactin can be obtained from Bacillus subtilis and glycolipids from e.g. Pseudomanas aeruginosa, Rhodococcus erythropolis, Mycobacterium species and Torulopsis bombicola (Desai and Banat, Microbiology and Molecular Biology Reviews, March, 1997, pp 47-64).

In EP 1 623 631 we have previously found that hydrophobins allow the production of aqueous foams with excellent stability to disproportionation and coalescence. Because hydrophobins are highly effective foaming agents, their presence in the fermentation medium presents a particular challenge for foam control.

Hydrophobins are a well-defined class of proteins (Wessels, 1997, Adv. Microb. Physio. 38: 1-45; Wosten, 2001, Annu Rev. Microbiol. 55: 625-646) capable of self-assembly at a hydrophobic/hydrophilic interface, and having a conserved sequence:

(SEQ ID NO. 1)

$$X_n\text{-C-}X_{5-9}\text{-C-C-}X_{11-39}\text{-C-}X_{8-23}\text{-C-}X_{5-9}\text{-C-C-}X_{6-18}\text{-C-}X_m$$

where X represents any amino acid, and n and m independently represent an integer. Typically, a hydrophobin has a length of up to 125 amino acids. The cysteine residues (C) in the conserved sequence are part of disulphide bridges. In the context of the present invention, the term hydrophobin has a wider meaning to include functionally equivalent proteins still displaying the characteristic of self-assembly at a hydrophobic-hydrophilic interface resulting in a protein film, such as proteins comprising the sequence:

(SEQ ID NO. 2)

$$X_n\text{-C-}X_{1-50}\text{-C-}X_{0-5}\text{-C-}X_{1-100}\text{-C-}X_{1-100}\text{-C-}X_{1-50}\text{-C-}X_{0-5}\text{-C-}X_{1-50}\text{-C-}X_m$$

or parts thereof still displaying the characteristic of self-assembly at a hydrophobic-hydrophilic interface resulting in a protein film. In accordance with the definition of the present invention, self-assembly can be detected by adsorbing the protein to Teflon and using Circular Dichroism to establish the presence of a secondary structure (in general, α-helix) (De Vocht et al., 1998, Biophys. J. 74: 2059-68).

The formation of a film can be established by incubating a Teflon sheet in the protein solution followed by at least three washes with water or buffer (Wosten et al., 1994, Embo. J. 13: 5848-54). The protein film can be visualised by any suitable method, such as labeling with a fluorescent marker or by the use of fluorescent antibodies, as is well established in the art, m and n typically have values ranging from 0 to 2000, but more usually m and n in total are less than 100 or 200. The definition of hydrophobin in the context of the present invention includes fusion proteins of a hydrophobin and another polypeptide as well as conjugates of hydrophobin and other molecules such as polysaccharides.

Hydrophobins identified to date are generally classed as either class I or class II. Both types have been identified in fungi as secreted proteins that self-assemble at hydrophobilic interfaces into amphipathic films. Assemblages of class I hydrophobins are generally relatively insoluble whereas those of class II hydrophobins readily dissolve in a variety of solvents. Preferably the hydrophobin is soluble in water, by which is meant that it is at least 0.1% soluble in water, preferably at least 0.5%. By at least 0.1% soluble is meant that no hydrophobin precipitates when 0.1 g of hydrophobin in 99.9 mL of water is subjected to 30,000 g centrifugation for 30 minutes at 20° C.

Hydrophobin-like proteins (e.g. "chaplins") have also been identified in filamentous bacteria, such as Actinomycete and Streptomyces sp. (WO01/74864; Talbot, 2003, Curr. Biol, 13: R696-R698). These bacterial proteins by contrast to fungal hydrophobins, may form only up to one disulphide bridge since they may have only two cysteine residues. Such proteins are an example of functional equivalents to hydrophobins having the consensus sequences shown in SEQ ID NOs. 1 and 2, and are within the scope of the present invention.

More than 34 genes coding for hydrophobins have been cloned, from over 16 fungal species (see for example WO96/41882 which gives the sequence of hydrophobins identified in Agaricus bisporus; and Wosten, 2001, Annu Rev. Microbiol. 55: 625-646). For the purpose of the invention hydrophobins possessing at least 80% identity at the amino acid level to a hydrophobin that naturally occurs are also embraced within the term "hydrophobins".

Antifoams

The term "antifoam" includes both antifoams which are usually added before foaming occurs and also those which are usually added once the foam has formed (sometimes known as defoamers). A definition of antifoams used in the present invention is found in "Foam and its mitigation in fermentation systems"—Beth Junker—Biotechnology Progress, 2007, 23, 768-784.

Fermentation Process

The fermentation to produce hydrophobin is carried out by culturing the host cell in a liquid fermentation medium within a bioreactor (e.g. an industrial fermenter). The composition of the medium (e.g. nutrients, carbon source etc.), temperature and pH are chosen to provide appropriate conditions for growth of the culture and/or production of the foaming agent. Air or oxygen-enriched air is normally sparged into the medium to provide oxygen for respiration of the culture.

The antifoam may be included in the initial medium composition and/or added as required through the period of the fermentation. Common practice is to employ a foam detection method, such as a conductivity probe, which automatically triggers addition of the antifoam. In the present invention, the antifoam is preferably present at a final concentration of from 0.1 to 20 g/L, more preferably from 1 to 10 g/L.

The fermenter temperature during step i), i.e. during fermentation, may be above or below the cloud point of the antifoam. Preferably the fermenter temperature is above the cloud point of the antifoam, since the antifoam is most effective at causing bubble coalescence and foam collapse above its cloud point. The fermenter temperature is generally chosen to achieve optimum conditions for growth of the host cells and/or production.

BRIEF DESCRIPTION OF THE INVENTION

It is the object of the invention to provide a process for extracting hydrophobin from a solution wherein carrageenan is added to the solution and the pH of the solution is brought below 3.5, preferably below 3.

In a first preferred embodiment of the invention, the solution is then filtered to produce a retentate and a filtrate, hydrophobin being recovered from the retentate. In a second preferred embodiment of the invention, the solution is submitted to a centrifugation step to produce a supernatant which is removed, leaving a remaining phase. Hydrophobin is then removed from the remaining phase.

Preferably, the process comprises the step of cultivating a host cell in a fermentation medium wherein the host cell extra-cellularly secretes hydrophobin; and the fermentation medium contains an antifoam. More preferably, the fermentation medium is aerated by sparging air or oxygen-enriched air into it.

Preferably the hydrophobin is HFBI or HFBII from Trichoderma reesei.

Preferably the host cell is a genetically-modified fungus, more preferably a yeast, most preferably Saccharomyces cerevisiae.

Preferably the ionic strength of the solution is below 0.5, preferably below 0.4, more preferably below 0.3, even more preferably below 0.2

Preferably, carrageenan is kappa or iota carrageenan, more preferably iota carrageenan.

Preferably also the carrageenan/hydrophobin ratio (w/w) is between 1:10 and 10:1, preferably above 1:5, more preferably above 1:1.

DETAILED DESCRIPTION OF THE INVENTION

The present invention will be further described in the following examples wherein the hydrophobin is always HFB II.

Example 1

Comparative

Starting concentration 145.4 μg/cm$^3$ of hydrophobin in 4.5 cm$^3$ of a 25 mM citric acid solution. The solution was filtered leading to a concentration in filtrate of 67.9 μg/cm$^3$ in 9 cm$^3$. There for 93% of the original hydrophobin filtered through.

Example 2

Comparative

Starting concentration 146.3 μg/cm$^3$ of hydrophobin in 4.5 cm$^3$ of a 25 mM sodium Citrate. The solution was filtered leading to a concentration in filtrate of 68.0 μg/cm$^3$ in 9 cm$^3$. Therefore again 93% of the original hydrophobin filtered through.

Example 3

Invention

Starting concentration 145.9 μg/cm$^3$ of hydrophobin in 4.5 cm$^3$ of a 25 mM citric acid solution+1% kappa carrageenan sheared gel. The solution was filtered leading to a concentration in filtrate of 3.8 μg/cm$^3$ hydrophobin in 9 cm$^3$.

Therefore, only 5% of the hydrophobin filtered through.

Then 9 cm$^3$ of 25 mM sodium citrate at pH 8 were passed through filter. The concentration in the filtrate was 40.9 μg/ml, therefore 56% of the original hydrophobin was recovered that way.

Example 4

Comparative

Starting concentration 145.9 μg/cm$^3$ of hydrophobin in 4.5 cm$^3$ of a 25 mM citric acid solution+1% kappa carrageenan sheared gel.

Then add 0.325 cm$^3$ NaOH (to go to pH 7.0) and filter

Concentration in filtrate=75.6 μg/cm$^3$ in 9 cm$^3$

Here, 100% of the hydrophobin ended in the filtrate despite the use of carrageenan, showing the importance of pH.

Example 5

Invention

Starting concentration 145.9 μg/cm$^3$ of hydrophobin in 4.5 cm$^3$ of a 25 mM citric acid solution+1% kappa carrageenan sheared gel.

Then add solid NaCl to give a concentration of 0.5M NaCl and filter. The concentration in filtrate is 50.9 μg/cm$^3$ in 9 cm$^3$. So, about 70% of the original amount of hydrophobin filtered through despite the right pH and the use of 1% kappa carrageenan sheared gel.

Then 9 cm$^3$ of 25 mM sodium citrate at pH 8 passed through filter leading to a concentration in filtrate of 13.8 μg/cm$^3$. Therefore, only 19% of the hydrophobin was recovered that way, showing the influence of the ionic strength on the whole process. The higher the ionic strength, the lower the recovery, everything else being equal.

Example 6a

Invention

Starting concentration 145.9 μg/cm$^3$ of hydrophobin in 4.5 cm$^3$ of a 25 mM citric acid solution+0.025% iota carrageenan.

The concentration in filtrate was 1.6 μg/cm$^3$ in 9 cm$^3$, only 2% of the original hydrophobin having passed through.

Then 9 cm$^3$ of 25 mM sodium citrate at pH 8 passed through filter, leading to a concentration in filtrate=29.5 μg/cm$^3$ Over 40% of the original hydrophobin was recovered.

Example 6b

Invention

Starting concentration 145.9 μg/cm$^3$ of hydrophobin in 4.5 cm$^3$ of a 25 mM citric acid solution+0.025% kappa carrageenan.

The concentration in filtrate was 28.4 μg/cm$^3$ in 9 cm$^3$, 39% of the original hydrophobin having passed through.

This example shows that iota carrageenan performs better that kappa carrageenan when retaining hydrophobin Example 7

Comparative

Starting concentration 145.9 μg/cm$^3$ of hydrophobin in 4.5 cm$^3$ of a 25 mM citric acid solution+1% sheared pectin.

The concentration in filtrate was 57.3 μg/cm$^3$ in 9 cm$^3$, representing 79% of the original hydrophobin, showing that pectin does not work.

Example 8

Comparative

Starting concentration 145.9 μg/cm$^3$ of hydrophobin in 4.5 cm$^3$ of a 25 mM citric acid and 1% N creamer 46.

The concentration in filtrate was 64.2 μg/cm$^3$ in 9 cm$^3$ representing 88% of the original hydrophobin, showing that hydrophobic starch does not work.

SEQUENCE LISTING

```
<160> NUMBER OF SEQ ID NOS: 2

<210> SEQ ID NO 1
<211> LENGTH: 4106
<212> TYPE: PRT
<213> ORGANISM: Artificial
<220> FEATURE:
<223> OTHER INFORMATION: Exemplary sequence used to illustrate
      invention.
<220> FEATURE:
<221> NAME/KEY: REPEAT
<222> LOCATION: (1)..(2000)
<223> OTHER INFORMATION: Xaa is any amino acid and can be shown 1 to
      2000 times.
<220> FEATURE:
<221> NAME/KEY: REPEAT
<222> LOCATION: (2002)..(2010)
<223> OTHER INFORMATION: Xaa is any amino acid and can be shown 5 to 9
      times.
<220> FEATURE:
<221> NAME/KEY: REPEAT
<222> LOCATION: (2013)..(2051)
<223> OTHER INFORMATION: Xaa is any amino acid and can be shown 11 to 39
      times.
```

```
<220> FEATURE:
<221> NAME/KEY: REPEAT
<222> LOCATION: (2053)..(2075)
<223> OTHER INFORMATION: Xaa is any amino acid and can be shown 8 to 23
      times.
<220> FEATURE:
<221> NAME/KEY: REPEAT
<222> LOCATION: (2077)..(2085)
<223> OTHER INFORMATION: Xaa is any amino acid and can be shown 5 to 9
      times.
<220> FEATURE:
<221> NAME/KEY: REPEAT
<222> LOCATION: (2088)..(2105)
<223> OTHER INFORMATION: Xaa is any amino acid and can be shown 6 to 18
      times.
<220> FEATURE:
<221> NAME/KEY: REPEAT
<222> LOCATION: (2107)..(4106)
<223> OTHER INFORMATION: indefinite repeats.  Xaa is any amino acid.

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
```

```
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa Xaa Xaa
    690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa Xaa
                725                 730                 735
```

-continued

```
Xaa Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa Xaa
        755                 760                 765

Xaa Xaa Xaa Xaa Xaa Xaa Xaa Xaa Xaa Xaa Xaa Xaa Xaa Xaa Xaa Xaa
    770                 775                 780

Xaa Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa Xaa
        835                 840                 845

Xaa Xaa Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa Xaa
                885                 890                 895

Xaa Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa Xaa
        915                 920                 925

Xaa Xaa Xaa Xaa Xaa Xaa Xaa Xaa Xaa Xaa Xaa Xaa Xaa Xaa Xaa Xaa
    930                 935                 940

Xaa Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa Xaa
                965                 970                 975

Xaa Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Xaa Xaa Xaa Xaa Xaa Xaa Xaa Xaa Xaa
        995                 1000                1005

Xaa Xaa Xaa Xaa Xaa Xaa Xaa Xaa Xaa Xaa Xaa Xaa Xaa Xaa Xaa Xaa
    1010                1015                1020

Xaa Xaa Xaa Xaa Xaa Xaa Xaa Xaa Xaa Xaa Xaa Xaa Xaa Xaa Xaa Xaa
1025                1030                1035                1040

Xaa Xaa Xaa Xaa Xaa Xaa Xaa Xaa Xaa Xaa Xaa Xaa Xaa Xaa Xaa Xaa
                1045                1050                1055

Xaa Xaa Xaa Xaa Xaa Xaa Xaa Xaa Xaa Xaa Xaa Xaa Xaa Xaa Xaa Xaa
            1060                1065                1070

Xaa Xaa Xaa Xaa Xaa Xaa Xaa Xaa Xaa Xaa Xaa Xaa Xaa Xaa Xaa Xaa
        1075                1080                1085

Xaa Xaa Xaa Xaa Xaa Xaa Xaa Xaa Xaa Xaa Xaa Xaa Xaa Xaa Xaa Xaa
    1090                1095                1100

Xaa Xaa Xaa Xaa Xaa Xaa Xaa Xaa Xaa Xaa Xaa Xaa Xaa Xaa Xaa Xaa
1105                1110                1115                1120

Xaa Xaa Xaa Xaa Xaa Xaa Xaa Xaa Xaa Xaa Xaa Xaa Xaa Xaa Xaa Xaa
                1125                1130                1135

Xaa Xaa Xaa Xaa Xaa Xaa Xaa Xaa Xaa Xaa Xaa Xaa Xaa Xaa Xaa Xaa
            1140                1145                1150

Xaa Xaa Xaa Xaa Xaa Xaa Xaa Xaa Xaa Xaa Xaa Xaa Xaa Xaa Xaa Xaa
        1155                1160                1165
```

```
Xaa Xaa Xaa Xaa Xaa Xaa Xaa Xaa Xaa Xaa Xaa Xaa Xaa Xaa Xaa Xaa
    1170                1175                1180

Xaa Xaa Xaa Xaa Xaa Xaa Xaa Xaa Xaa Xaa Xaa Xaa Xaa Xaa Xaa Xaa
1185                1190                1195                1200

Xaa Xaa Xaa Xaa Xaa Xaa Xaa Xaa Xaa Xaa Xaa Xaa Xaa Xaa Xaa Xaa
                1205                1210                1215

Xaa Xaa Xaa Xaa Xaa Xaa Xaa Xaa Xaa Xaa Xaa Xaa Xaa Xaa Xaa Xaa
            1220                1225                1230

Xaa Xaa Xaa Xaa Xaa Xaa Xaa Xaa Xaa Xaa Xaa Xaa Xaa Xaa Xaa Xaa
        1235                1240                1245

Xaa Xaa Xaa Xaa Xaa Xaa Xaa Xaa Xaa Xaa Xaa Xaa Xaa Xaa Xaa Xaa
    1250                1255                1260

Xaa Xaa Xaa Xaa Xaa Xaa Xaa Xaa Xaa Xaa Xaa Xaa Xaa Xaa Xaa Xaa
1265                1270                1275                1280

Xaa Xaa Xaa Xaa Xaa Xaa Xaa Xaa Xaa Xaa Xaa Xaa Xaa Xaa Xaa Xaa
                1285                1290                1295

Xaa Xaa Xaa Xaa Xaa Xaa Xaa Xaa Xaa Xaa Xaa Xaa Xaa Xaa Xaa Xaa
            1300                1305                1310

Xaa Xaa Xaa Xaa Xaa Xaa Xaa Xaa Xaa Xaa Xaa Xaa Xaa Xaa Xaa Xaa
        1315                1320                1325

Xaa Xaa Xaa Xaa Xaa Xaa Xaa Xaa Xaa Xaa Xaa Xaa Xaa Xaa Xaa Xaa
    1330                1335                1340

Xaa Xaa Xaa Xaa Xaa Xaa Xaa Xaa Xaa Xaa Xaa Xaa Xaa Xaa Xaa Xaa
1345                1350                1355                1360

Xaa Xaa Xaa Xaa Xaa Xaa Xaa Xaa Xaa Xaa Xaa Xaa Xaa Xaa Xaa Xaa
                1365                1370                1375

Xaa Xaa Xaa Xaa Xaa Xaa Xaa Xaa Xaa Xaa Xaa Xaa Xaa Xaa Xaa Xaa
            1380                1385                1390

Xaa Xaa Xaa Xaa Xaa Xaa Xaa Xaa Xaa Xaa Xaa Xaa Xaa Xaa Xaa Xaa
        1395                1400                1405

Xaa Xaa Xaa Xaa Xaa Xaa Xaa Xaa Xaa Xaa Xaa Xaa Xaa Xaa Xaa Xaa
    1410                1415                1420

Xaa Xaa Xaa Xaa Xaa Xaa Xaa Xaa Xaa Xaa Xaa Xaa Xaa Xaa Xaa Xaa
1425                1430                1435                1440

Xaa Xaa Xaa Xaa Xaa Xaa Xaa Xaa Xaa Xaa Xaa Xaa Xaa Xaa Xaa Xaa
                1445                1450                1455

Xaa Xaa Xaa Xaa Xaa Xaa Xaa Xaa Xaa Xaa Xaa Xaa Xaa Xaa Xaa Xaa
            1460                1465                1470

Xaa Xaa Xaa Xaa Xaa Xaa Xaa Xaa Xaa Xaa Xaa Xaa Xaa Xaa Xaa Xaa
        1475                1480                1485

Xaa Xaa Xaa Xaa Xaa Xaa Xaa Xaa Xaa Xaa Xaa Xaa Xaa Xaa Xaa Xaa
    1490                1495                1500

Xaa Xaa Xaa Xaa Xaa Xaa Xaa Xaa Xaa Xaa Xaa Xaa Xaa Xaa Xaa Xaa
1505                1510                1515                1520

Xaa Xaa Xaa Xaa Xaa Xaa Xaa Xaa Xaa Xaa Xaa Xaa Xaa Xaa Xaa Xaa
                1525                1530                1535

Xaa Xaa Xaa Xaa Xaa Xaa Xaa Xaa Xaa Xaa Xaa Xaa Xaa Xaa Xaa Xaa
            1540                1545                1550

Xaa Xaa Xaa Xaa Xaa Xaa Xaa Xaa Xaa Xaa Xaa Xaa Xaa Xaa Xaa Xaa
        1555                1560                1565

Xaa Xaa Xaa Xaa Xaa Xaa Xaa Xaa Xaa Xaa Xaa Xaa Xaa Xaa Xaa Xaa
    1570                1575                1580

Xaa Xaa Xaa Xaa Xaa Xaa Xaa Xaa Xaa Xaa Xaa Xaa Xaa Xaa Xaa Xaa
```

```
1585                1590                1595                1600

Xaa Xaa Xaa Xaa Xaa Xaa Xaa Xaa Xaa Xaa Xaa Xaa Xaa Xaa Xaa Xaa
                1605                1610                1615

Xaa Xaa Xaa Xaa Xaa Xaa Xaa Xaa Xaa Xaa Xaa Xaa Xaa Xaa Xaa Xaa
            1620                1625                1630

Xaa Xaa Xaa Xaa Xaa Xaa Xaa Xaa Xaa Xaa Xaa Xaa Xaa Xaa Xaa Xaa
        1635                1640                1645

Xaa Xaa Xaa Xaa Xaa Xaa Xaa Xaa Xaa Xaa Xaa Xaa Xaa Xaa Xaa Xaa
    1650                1655                1660

Xaa Xaa Xaa Xaa Xaa Xaa Xaa Xaa Xaa Xaa Xaa Xaa Xaa Xaa Xaa Xaa
1665                1670                1675                1680

Xaa Xaa Xaa Xaa Xaa Xaa Xaa Xaa Xaa Xaa Xaa Xaa Xaa Xaa Xaa Xaa
                1685                1690                1695

Xaa Xaa Xaa Xaa Xaa Xaa Xaa Xaa Xaa Xaa Xaa Xaa Xaa Xaa Xaa Xaa
            1700                1705                1710

Xaa Xaa Xaa Xaa Xaa Xaa Xaa Xaa Xaa Xaa Xaa Xaa Xaa Xaa Xaa Xaa
        1715                1720                1725

Xaa Xaa Xaa Xaa Xaa Xaa Xaa Xaa Xaa Xaa Xaa Xaa Xaa Xaa Xaa Xaa
    1730                1735                1740

Xaa Xaa Xaa Xaa Xaa Xaa Xaa Xaa Xaa Xaa Xaa Xaa Xaa Xaa Xaa Xaa
1745                1750                1755                1760

Xaa Xaa Xaa Xaa Xaa Xaa Xaa Xaa Xaa Xaa Xaa Xaa Xaa Xaa Xaa Xaa
                1765                1770                1775

Xaa Xaa Xaa Xaa Xaa Xaa Xaa Xaa Xaa Xaa Xaa Xaa Xaa Xaa Xaa Xaa
            1780                1785                1790

Xaa Xaa Xaa Xaa Xaa Xaa Xaa Xaa Xaa Xaa Xaa Xaa Xaa Xaa Xaa Xaa
        1795                1800                1805

Xaa Xaa Xaa Xaa Xaa Xaa Xaa Xaa Xaa Xaa Xaa Xaa Xaa Xaa Xaa Xaa
    1810                1815                1820

Xaa Xaa Xaa Xaa Xaa Xaa Xaa Xaa Xaa Xaa Xaa Xaa Xaa Xaa Xaa Xaa
1825                1830                1835                1840

Xaa Xaa Xaa Xaa Xaa Xaa Xaa Xaa Xaa Xaa Xaa Xaa Xaa Xaa Xaa Xaa
                1845                1850                1855

Xaa Xaa Xaa Xaa Xaa Xaa Xaa Xaa Xaa Xaa Xaa Xaa Xaa Xaa Xaa Xaa
            1860                1865                1870

Xaa Xaa Xaa Xaa Xaa Xaa Xaa Xaa Xaa Xaa Xaa Xaa Xaa Xaa Xaa Xaa
        1875                1880                1885

Xaa Xaa Xaa Xaa Xaa Xaa Xaa Xaa Xaa Xaa Xaa Xaa Xaa Xaa Xaa Xaa
    1890                1895                1900

Xaa Xaa Xaa Xaa Xaa Xaa Xaa Xaa Xaa Xaa Xaa Xaa Xaa Xaa Xaa Xaa
1905                1910                1915                1920

Xaa Xaa Xaa Xaa Xaa Xaa Xaa Xaa Xaa Xaa Xaa Xaa Xaa Xaa Xaa Xaa
                1925                1930                1935

Xaa Xaa Xaa Xaa Xaa Xaa Xaa Xaa Xaa Xaa Xaa Xaa Xaa Xaa Xaa Xaa
            1940                1945                1950

Xaa Xaa Xaa Xaa Xaa Xaa Xaa Xaa Xaa Xaa Xaa Xaa Xaa Xaa Xaa Xaa
        1955                1960                1965

Xaa Xaa Xaa Xaa Xaa Xaa Xaa Xaa Xaa Xaa Xaa Xaa Xaa Xaa Xaa Xaa
    1970                1975                1980

Xaa Xaa Xaa Xaa Xaa Xaa Xaa Xaa Xaa Xaa Xaa Xaa Xaa Xaa Xaa Xaa
1985                1990                1995                2000

Cys Xaa Xaa Xaa Xaa Xaa Xaa Xaa Xaa Xaa Cys Cys Xaa Xaa Xaa Xaa
                2005                2010                2015
```

```
Xaa Xaa Xaa Xaa Xaa Xaa Xaa Xaa Xaa Xaa Xaa Xaa Xaa Xaa Xaa Xaa
            2020                2025                2030

Xaa Xaa Xaa Xaa Xaa Xaa Xaa Xaa Xaa Xaa Xaa Xaa Xaa Xaa Xaa Xaa
        2035                2040                2045

Xaa Xaa Xaa Cys Xaa Xaa Xaa Xaa Xaa Xaa Xaa Xaa Xaa Xaa Xaa Xaa
    2050                2055                2060

Xaa Xaa Xaa Xaa Xaa Xaa Xaa Xaa Xaa Xaa Xaa Cys Xaa Xaa Xaa Xaa
2065                2070                2075                2080

Xaa Xaa Xaa Xaa Xaa Cys Cys Xaa Xaa Xaa Xaa Xaa Xaa Xaa Xaa Xaa
                2085                2090                2095

Xaa Xaa Xaa Xaa Xaa Xaa Xaa Xaa Xaa Cys Xaa Xaa Xaa Xaa Xaa Xaa
            2100                2105                2110

Xaa Xaa Xaa Xaa Xaa Xaa Xaa Xaa Xaa Xaa Xaa Xaa Xaa Xaa Xaa Xaa
        2115                2120                2125

Xaa Xaa Xaa Xaa Xaa Xaa Xaa Xaa Xaa Xaa Xaa Xaa Xaa Xaa Xaa Xaa
    2130                2135                2140

Xaa Xaa Xaa Xaa Xaa Xaa Xaa Xaa Xaa Xaa Xaa Xaa Xaa Xaa Xaa Xaa
2145                2150                2155                2160

Xaa Xaa Xaa Xaa Xaa Xaa Xaa Xaa Xaa Xaa Xaa Xaa Xaa Xaa Xaa Xaa
                2165                2170                2175

Xaa Xaa Xaa Xaa Xaa Xaa Xaa Xaa Xaa Xaa Xaa Xaa Xaa Xaa Xaa Xaa
            2180                2185                2190

Xaa Xaa Xaa Xaa Xaa Xaa Xaa Xaa Xaa Xaa Xaa Xaa Xaa Xaa Xaa Xaa
        2195                2200                2205

Xaa Xaa Xaa Xaa Xaa Xaa Xaa Xaa Xaa Xaa Xaa Xaa Xaa Xaa Xaa Xaa
    2210                2215                2220

Xaa Xaa Xaa Xaa Xaa Xaa Xaa Xaa Xaa Xaa Xaa Xaa Xaa Xaa Xaa Xaa
2225                2230                2235                2240

Xaa Xaa Xaa Xaa Xaa Xaa Xaa Xaa Xaa Xaa Xaa Xaa Xaa Xaa Xaa Xaa
                2245                2250                2255

Xaa Xaa Xaa Xaa Xaa Xaa Xaa Xaa Xaa Xaa Xaa Xaa Xaa Xaa Xaa Xaa
            2260                2265                2270

Xaa Xaa Xaa Xaa Xaa Xaa Xaa Xaa Xaa Xaa Xaa Xaa Xaa Xaa Xaa Xaa
        2275                2280                2285

Xaa Xaa Xaa Xaa Xaa Xaa Xaa Xaa Xaa Xaa Xaa Xaa Xaa Xaa Xaa Xaa
    2290                2295                2300

Xaa Xaa Xaa Xaa Xaa Xaa Xaa Xaa Xaa Xaa Xaa Xaa Xaa Xaa Xaa Xaa
2305                2310                2315                2320

Xaa Xaa Xaa Xaa Xaa Xaa Xaa Xaa Xaa Xaa Xaa Xaa Xaa Xaa Xaa Xaa
                2325                2330                2335

Xaa Xaa Xaa Xaa Xaa Xaa Xaa Xaa Xaa Xaa Xaa Xaa Xaa Xaa Xaa Xaa
            2340                2345                2350

Xaa Xaa Xaa Xaa Xaa Xaa Xaa Xaa Xaa Xaa Xaa Xaa Xaa Xaa Xaa Xaa
        2355                2360                2365

Xaa Xaa Xaa Xaa Xaa Xaa Xaa Xaa Xaa Xaa Xaa Xaa Xaa Xaa Xaa Xaa
    2370                2375                2380

Xaa Xaa Xaa Xaa Xaa Xaa Xaa Xaa Xaa Xaa Xaa Xaa Xaa Xaa Xaa Xaa
2385                2390                2395                2400

Xaa Xaa Xaa Xaa Xaa Xaa Xaa Xaa Xaa Xaa Xaa Xaa Xaa Xaa Xaa Xaa
                2405                2410                2415

Xaa Xaa Xaa Xaa Xaa Xaa Xaa Xaa Xaa Xaa Xaa Xaa Xaa Xaa Xaa Xaa
            2420                2425                2430

Xaa Xaa Xaa Xaa Xaa Xaa Xaa Xaa Xaa Xaa Xaa Xaa Xaa Xaa Xaa Xaa
        2435                2440                2445
```

```
Xaa Xaa Xaa Xaa Xaa Xaa Xaa Xaa Xaa Xaa Xaa Xaa Xaa Xaa Xaa Xaa
    2450                2455                2460

Xaa Xaa Xaa Xaa Xaa Xaa Xaa Xaa Xaa Xaa Xaa Xaa Xaa Xaa Xaa Xaa
2465                2470                2475                2480

Xaa Xaa Xaa Xaa Xaa Xaa Xaa Xaa Xaa Xaa Xaa Xaa Xaa Xaa Xaa Xaa
                2485                2490                2495

Xaa Xaa Xaa Xaa Xaa Xaa Xaa Xaa Xaa Xaa Xaa Xaa Xaa Xaa Xaa Xaa
            2500                2505                2510

Xaa Xaa Xaa Xaa Xaa Xaa Xaa Xaa Xaa Xaa Xaa Xaa Xaa Xaa Xaa Xaa
        2515                2520                2525

Xaa Xaa Xaa Xaa Xaa Xaa Xaa Xaa Xaa Xaa Xaa Xaa Xaa Xaa Xaa Xaa
    2530                2535                2540

Xaa Xaa Xaa Xaa Xaa Xaa Xaa Xaa Xaa Xaa Xaa Xaa Xaa Xaa Xaa Xaa
2545                2550                2555                2560

Xaa Xaa Xaa Xaa Xaa Xaa Xaa Xaa Xaa Xaa Xaa Xaa Xaa Xaa Xaa Xaa
                2565                2570                2575

Xaa Xaa Xaa Xaa Xaa Xaa Xaa Xaa Xaa Xaa Xaa Xaa Xaa Xaa Xaa Xaa
            2580                2585                2590

Xaa Xaa Xaa Xaa Xaa Xaa Xaa Xaa Xaa Xaa Xaa Xaa Xaa Xaa Xaa Xaa
        2595                2600                2605

Xaa Xaa Xaa Xaa Xaa Xaa Xaa Xaa Xaa Xaa Xaa Xaa Xaa Xaa Xaa Xaa
    2610                2615                2620

Xaa Xaa Xaa Xaa Xaa Xaa Xaa Xaa Xaa Xaa Xaa Xaa Xaa Xaa Xaa Xaa
2625                2630                2635                2640

Xaa Xaa Xaa Xaa Xaa Xaa Xaa Xaa Xaa Xaa Xaa Xaa Xaa Xaa Xaa Xaa
                2645                2650                2655

Xaa Xaa Xaa Xaa Xaa Xaa Xaa Xaa Xaa Xaa Xaa Xaa Xaa Xaa Xaa Xaa
            2660                2665                2670

Xaa Xaa Xaa Xaa Xaa Xaa Xaa Xaa Xaa Xaa Xaa Xaa Xaa Xaa Xaa Xaa
        2675                2680                2685

Xaa Xaa Xaa Xaa Xaa Xaa Xaa Xaa Xaa Xaa Xaa Xaa Xaa Xaa Xaa Xaa
    2690                2695                2700

Xaa Xaa Xaa Xaa Xaa Xaa Xaa Xaa Xaa Xaa Xaa Xaa Xaa Xaa Xaa Xaa
2705                2710                2715                2720

Xaa Xaa Xaa Xaa Xaa Xaa Xaa Xaa Xaa Xaa Xaa Xaa Xaa Xaa Xaa Xaa
                2725                2730                2735

Xaa Xaa Xaa Xaa Xaa Xaa Xaa Xaa Xaa Xaa Xaa Xaa Xaa Xaa Xaa Xaa
            2740                2745                2750

Xaa Xaa Xaa Xaa Xaa Xaa Xaa Xaa Xaa Xaa Xaa Xaa Xaa Xaa Xaa Xaa
        2755                2760                2765

Xaa Xaa Xaa Xaa Xaa Xaa Xaa Xaa Xaa Xaa Xaa Xaa Xaa Xaa Xaa Xaa
    2770                2775                2780

Xaa Xaa Xaa Xaa Xaa Xaa Xaa Xaa Xaa Xaa Xaa Xaa Xaa Xaa Xaa Xaa
2785                2790                2795                2800

Xaa Xaa Xaa Xaa Xaa Xaa Xaa Xaa Xaa Xaa Xaa Xaa Xaa Xaa Xaa Xaa
                2805                2810                2815

Xaa Xaa Xaa Xaa Xaa Xaa Xaa Xaa Xaa Xaa Xaa Xaa Xaa Xaa Xaa Xaa
            2820                2825                2830

Xaa Xaa Xaa Xaa Xaa Xaa Xaa Xaa Xaa Xaa Xaa Xaa Xaa Xaa Xaa Xaa
        2835                2840                2845

Xaa Xaa Xaa Xaa Xaa Xaa Xaa Xaa Xaa Xaa Xaa Xaa Xaa Xaa Xaa Xaa
    2850                2855                2860

Xaa Xaa Xaa Xaa Xaa Xaa Xaa Xaa Xaa Xaa Xaa Xaa Xaa Xaa Xaa Xaa
```

```
2865                2870                2875                2880

Xaa Xaa Xaa Xaa Xaa Xaa Xaa Xaa Xaa Xaa Xaa Xaa Xaa Xaa Xaa Xaa
                2885                2890                2895

Xaa Xaa Xaa Xaa Xaa Xaa Xaa Xaa Xaa Xaa Xaa Xaa Xaa Xaa Xaa Xaa
            2900                2905                2910

Xaa Xaa Xaa Xaa Xaa Xaa Xaa Xaa Xaa Xaa Xaa Xaa Xaa Xaa Xaa Xaa
        2915                2920                2925

Xaa Xaa Xaa Xaa Xaa Xaa Xaa Xaa Xaa Xaa Xaa Xaa Xaa Xaa Xaa Xaa
    2930                2935                2940

Xaa Xaa Xaa Xaa Xaa Xaa Xaa Xaa Xaa Xaa Xaa Xaa Xaa Xaa Xaa Xaa
2945                2950                2955                2960

Xaa Xaa Xaa Xaa Xaa Xaa Xaa Xaa Xaa Xaa Xaa Xaa Xaa Xaa Xaa Xaa
                2965                2970                2975

Xaa Xaa Xaa Xaa Xaa Xaa Xaa Xaa Xaa Xaa Xaa Xaa Xaa Xaa Xaa Xaa
            2980                2985                2990

Xaa Xaa Xaa Xaa Xaa Xaa Xaa Xaa Xaa Xaa Xaa Xaa Xaa Xaa Xaa Xaa
        2995                3000                3005

Xaa Xaa Xaa Xaa Xaa Xaa Xaa Xaa Xaa Xaa Xaa Xaa Xaa Xaa Xaa Xaa
    3010                3015                3020

Xaa Xaa Xaa Xaa Xaa Xaa Xaa Xaa Xaa Xaa Xaa Xaa Xaa Xaa Xaa Xaa
3025                3030                3035                3040

Xaa Xaa Xaa Xaa Xaa Xaa Xaa Xaa Xaa Xaa Xaa Xaa Xaa Xaa Xaa Xaa
                3045                3050                3055

Xaa Xaa Xaa Xaa Xaa Xaa Xaa Xaa Xaa Xaa Xaa Xaa Xaa Xaa Xaa Xaa
            3060                3065                3070

Xaa Xaa Xaa Xaa Xaa Xaa Xaa Xaa Xaa Xaa Xaa Xaa Xaa Xaa Xaa Xaa
        3075                3080                3085

Xaa Xaa Xaa Xaa Xaa Xaa Xaa Xaa Xaa Xaa Xaa Xaa Xaa Xaa Xaa Xaa
    3090                3095                3100

Xaa Xaa Xaa Xaa Xaa Xaa Xaa Xaa Xaa Xaa Xaa Xaa Xaa Xaa Xaa Xaa
3105                3110                3115                3120

Xaa Xaa Xaa Xaa Xaa Xaa Xaa Xaa Xaa Xaa Xaa Xaa Xaa Xaa Xaa Xaa
                3125                3130                3135

Xaa Xaa Xaa Xaa Xaa Xaa Xaa Xaa Xaa Xaa Xaa Xaa Xaa Xaa Xaa Xaa
            3140                3145                3150

Xaa Xaa Xaa Xaa Xaa Xaa Xaa Xaa Xaa Xaa Xaa Xaa Xaa Xaa Xaa Xaa
        3155                3160                3165

Xaa Xaa Xaa Xaa Xaa Xaa Xaa Xaa Xaa Xaa Xaa Xaa Xaa Xaa Xaa Xaa
    3170                3175                3180

Xaa Xaa Xaa Xaa Xaa Xaa Xaa Xaa Xaa Xaa Xaa Xaa Xaa Xaa Xaa Xaa
3185                3190                3195                3200

Xaa Xaa Xaa Xaa Xaa Xaa Xaa Xaa Xaa Xaa Xaa Xaa Xaa Xaa Xaa Xaa
                3205                3210                3215

Xaa Xaa Xaa Xaa Xaa Xaa Xaa Xaa Xaa Xaa Xaa Xaa Xaa Xaa Xaa Xaa
            3220                3225                3230

Xaa Xaa Xaa Xaa Xaa Xaa Xaa Xaa Xaa Xaa Xaa Xaa Xaa Xaa Xaa Xaa
        3235                3240                3245

Xaa Xaa Xaa Xaa Xaa Xaa Xaa Xaa Xaa Xaa Xaa Xaa Xaa Xaa Xaa Xaa
    3250                3255                3260

Xaa Xaa Xaa Xaa Xaa Xaa Xaa Xaa Xaa Xaa Xaa Xaa Xaa Xaa Xaa Xaa
3265                3270                3275                3280

Xaa Xaa Xaa Xaa Xaa Xaa Xaa Xaa Xaa Xaa Xaa Xaa Xaa Xaa Xaa Xaa
                3285                3290                3295
```

```
Xaa Xaa Xaa Xaa Xaa Xaa Xaa Xaa Xaa Xaa Xaa Xaa Xaa Xaa Xaa Xaa
            3300                3305                3310

Xaa Xaa Xaa Xaa Xaa Xaa Xaa Xaa Xaa Xaa Xaa Xaa Xaa Xaa Xaa Xaa
        3315                3320                3325

Xaa Xaa Xaa Xaa Xaa Xaa Xaa Xaa Xaa Xaa Xaa Xaa Xaa Xaa Xaa Xaa
    3330                3335                3340

Xaa Xaa Xaa Xaa Xaa Xaa Xaa Xaa Xaa Xaa Xaa Xaa Xaa Xaa Xaa Xaa
3345                3350                3355                3360

Xaa Xaa Xaa Xaa Xaa Xaa Xaa Xaa Xaa Xaa Xaa Xaa Xaa Xaa Xaa Xaa
                3365                3370                3375

Xaa Xaa Xaa Xaa Xaa Xaa Xaa Xaa Xaa Xaa Xaa Xaa Xaa Xaa Xaa Xaa
            3380                3385                3390

Xaa Xaa Xaa Xaa Xaa Xaa Xaa Xaa Xaa Xaa Xaa Xaa Xaa Xaa Xaa Xaa
        3395                3400                3405

Xaa Xaa Xaa Xaa Xaa Xaa Xaa Xaa Xaa Xaa Xaa Xaa Xaa Xaa Xaa Xaa
    3410                3415                3420

Xaa Xaa Xaa Xaa Xaa Xaa Xaa Xaa Xaa Xaa Xaa Xaa Xaa Xaa Xaa Xaa
3425                3430                3435                3440

Xaa Xaa Xaa Xaa Xaa Xaa Xaa Xaa Xaa Xaa Xaa Xaa Xaa Xaa Xaa Xaa
                3445                3450                3455

Xaa Xaa Xaa Xaa Xaa Xaa Xaa Xaa Xaa Xaa Xaa Xaa Xaa Xaa Xaa Xaa
            3460                3465                3470

Xaa Xaa Xaa Xaa Xaa Xaa Xaa Xaa Xaa Xaa Xaa Xaa Xaa Xaa Xaa Xaa
        3475                3480                3485

Xaa Xaa Xaa Xaa Xaa Xaa Xaa Xaa Xaa Xaa Xaa Xaa Xaa Xaa Xaa Xaa
    3490                3495                3500

Xaa Xaa Xaa Xaa Xaa Xaa Xaa Xaa Xaa Xaa Xaa Xaa Xaa Xaa Xaa Xaa
3505                3510                3515                3520

Xaa Xaa Xaa Xaa Xaa Xaa Xaa Xaa Xaa Xaa Xaa Xaa Xaa Xaa Xaa Xaa
                3525                3530                3535

Xaa Xaa Xaa Xaa Xaa Xaa Xaa Xaa Xaa Xaa Xaa Xaa Xaa Xaa Xaa Xaa
            3540                3545                3550

Xaa Xaa Xaa Xaa Xaa Xaa Xaa Xaa Xaa Xaa Xaa Xaa Xaa Xaa Xaa Xaa
        3555                3560                3565

Xaa Xaa Xaa Xaa Xaa Xaa Xaa Xaa Xaa Xaa Xaa Xaa Xaa Xaa Xaa Xaa
    3570                3575                3580

Xaa Xaa Xaa Xaa Xaa Xaa Xaa Xaa Xaa Xaa Xaa Xaa Xaa Xaa Xaa Xaa
3585                3590                3595                3600

Xaa Xaa Xaa Xaa Xaa Xaa Xaa Xaa Xaa Xaa Xaa Xaa Xaa Xaa Xaa Xaa
                3605                3610                3615

Xaa Xaa Xaa Xaa Xaa Xaa Xaa Xaa Xaa Xaa Xaa Xaa Xaa Xaa Xaa Xaa
            3620                3625                3630

Xaa Xaa Xaa Xaa Xaa Xaa Xaa Xaa Xaa Xaa Xaa Xaa Xaa Xaa Xaa Xaa
        3635                3640                3645

Xaa Xaa Xaa Xaa Xaa Xaa Xaa Xaa Xaa Xaa Xaa Xaa Xaa Xaa Xaa Xaa
    3650                3655                3660

Xaa Xaa Xaa Xaa Xaa Xaa Xaa Xaa Xaa Xaa Xaa Xaa Xaa Xaa Xaa Xaa
3665                3670                3675                3680

Xaa Xaa Xaa Xaa Xaa Xaa Xaa Xaa Xaa Xaa Xaa Xaa Xaa Xaa Xaa Xaa
                3685                3690                3695

Xaa Xaa Xaa Xaa Xaa Xaa Xaa Xaa Xaa Xaa Xaa Xaa Xaa Xaa Xaa Xaa
            3700                3705                3710

Xaa Xaa Xaa Xaa Xaa Xaa Xaa Xaa Xaa Xaa Xaa Xaa Xaa Xaa Xaa Xaa
        3715                3720                3725
```

```
Xaa Xaa Xaa Xaa Xaa Xaa Xaa Xaa Xaa Xaa Xaa Xaa Xaa Xaa Xaa Xaa
    3730                3735                3740

Xaa Xaa Xaa Xaa Xaa Xaa Xaa Xaa Xaa Xaa Xaa Xaa Xaa Xaa Xaa Xaa
3745                3750                3755                3760

Xaa Xaa Xaa Xaa Xaa Xaa Xaa Xaa Xaa Xaa Xaa Xaa Xaa Xaa Xaa Xaa
                3765                3770                3775

Xaa Xaa Xaa Xaa Xaa Xaa Xaa Xaa Xaa Xaa Xaa Xaa Xaa Xaa Xaa Xaa
            3780                3785                3790

Xaa Xaa Xaa Xaa Xaa Xaa Xaa Xaa Xaa Xaa Xaa Xaa Xaa Xaa Xaa Xaa
        3795                3800                3805

Xaa Xaa Xaa Xaa Xaa Xaa Xaa Xaa Xaa Xaa Xaa Xaa Xaa Xaa Xaa Xaa
    3810                3815                3820

Xaa Xaa Xaa Xaa Xaa Xaa Xaa Xaa Xaa Xaa Xaa Xaa Xaa Xaa Xaa Xaa
3825                3830                3835                3840

Xaa Xaa Xaa Xaa Xaa Xaa Xaa Xaa Xaa Xaa Xaa Xaa Xaa Xaa Xaa Xaa
                3845                3850                3855

Xaa Xaa Xaa Xaa Xaa Xaa Xaa Xaa Xaa Xaa Xaa Xaa Xaa Xaa Xaa Xaa
            3860                3865                3870

Xaa Xaa Xaa Xaa Xaa Xaa Xaa Xaa Xaa Xaa Xaa Xaa Xaa Xaa Xaa Xaa
        3875                3880                3885

Xaa Xaa Xaa Xaa Xaa Xaa Xaa Xaa Xaa Xaa Xaa Xaa Xaa Xaa Xaa Xaa
    3890                3895                3900

Xaa Xaa Xaa Xaa Xaa Xaa Xaa Xaa Xaa Xaa Xaa Xaa Xaa Xaa Xaa Xaa
3905                3910                3915                3920

Xaa Xaa Xaa Xaa Xaa Xaa Xaa Xaa Xaa Xaa Xaa Xaa Xaa Xaa Xaa Xaa
                3925                3930                3935

Xaa Xaa Xaa Xaa Xaa Xaa Xaa Xaa Xaa Xaa Xaa Xaa Xaa Xaa Xaa Xaa
            3940                3945                3950

Xaa Xaa Xaa Xaa Xaa Xaa Xaa Xaa Xaa Xaa Xaa Xaa Xaa Xaa Xaa Xaa
        3955                3960                3965

Xaa Xaa Xaa Xaa Xaa Xaa Xaa Xaa Xaa Xaa Xaa Xaa Xaa Xaa Xaa Xaa
    3970                3975                3980

Xaa Xaa Xaa Xaa Xaa Xaa Xaa Xaa Xaa Xaa Xaa Xaa Xaa Xaa Xaa Xaa
3985                3990                3995                4000

Xaa Xaa Xaa Xaa Xaa Xaa Xaa Xaa Xaa Xaa Xaa Xaa Xaa Xaa Xaa Xaa
                4005                4010                4015

Xaa Xaa Xaa Xaa Xaa Xaa Xaa Xaa Xaa Xaa Xaa Xaa Xaa Xaa Xaa Xaa
            4020                4025                4030

Xaa Xaa Xaa Xaa Xaa Xaa Xaa Xaa Xaa Xaa Xaa Xaa Xaa Xaa Xaa Xaa
        4035                4040                4045

Xaa Xaa Xaa Xaa Xaa Xaa Xaa Xaa Xaa Xaa Xaa Xaa Xaa Xaa Xaa Xaa
    4050                4055                4060

Xaa Xaa Xaa Xaa Xaa Xaa Xaa Xaa Xaa Xaa Xaa Xaa Xaa Xaa Xaa Xaa
4065                4070                4075                4080

Xaa Xaa Xaa Xaa Xaa Xaa Xaa Xaa Xaa Xaa Xaa Xaa Xaa Xaa Xaa Xaa
                4085                4090                4095

Xaa Xaa Xaa Xaa Xaa Xaa Xaa Xaa Xaa Xaa
            4100                4105


<210> SEQ ID NO 2
<211> LENGTH: 4368
<212> TYPE: PRT
<213> ORGANISM: Artificial
<220> FEATURE:
<223> OTHER INFORMATION: Exemplary sequence used to illustrate
```

```
      invention.
<220> FEATURE:
<221> NAME/KEY: REPEAT
<222> LOCATION: (1)..(2000)
<223> OTHER INFORMATION: Xaa is any amino acid and can be shown 1 to
      2000 times.
<220> FEATURE:
<221> NAME/KEY: REPEAT
<222> LOCATION: (2002)..(2051)
<223> OTHER INFORMATION: Xaa is any amino acid and can be shown 1 to 50
      times.
<220> FEATURE:
<221> NAME/KEY: REPEAT
<222> LOCATION: (2053)..(2057)
<223> OTHER INFORMATION: Xaa is any amino acid and can be shown 0 to 5
      times.
<220> FEATURE:
<221> NAME/KEY: REPEAT
<222> LOCATION: (2059)..(2158)
<223> OTHER INFORMATION: Xaa is any amino acid and can be shown 1 to 100
      times.
<220> FEATURE:
<221> NAME/KEY: REPEAT
<222> LOCATION: (2160)..(2259)
<223> OTHER INFORMATION: Xaa is any amino acid and can be shown 1 to 100
      times.
<220> FEATURE:
<221> NAME/KEY: REPEAT
<222> LOCATION: (2261)..(2310)
<223> OTHER INFORMATION: Xaa is any amino acid and can be shown 1 to 50
      times.
<220> FEATURE:
<221> NAME/KEY: REPEAT
<222> LOCATION: (2312)..(2316)
<223> OTHER INFORMATION: Xaa is any amino acid and can be shown 0 to 5
      times.
<220> FEATURE:
<221> NAME/KEY: REPEAT
<222> LOCATION: (2318)..(2367)
<223> OTHER INFORMATION: Xaa is any amino acid and can be shown 1 to 50
      times.
<220> FEATURE:
<221> NAME/KEY: REPEAT
<222> LOCATION: (2369)..(4368)
<223> OTHER INFORMATION: Xaa is any amino acid and can be shown 1 to
      2000 times.

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
```

```
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590
```

-continued

```
Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa Xaa Xaa
    690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa Xaa
                725                 730                 735

Xaa Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa Xaa
        755                 760                 765

Xaa Xaa Xaa Xaa Xaa Xaa Xaa Xaa Xaa Xaa Xaa Xaa Xaa Xaa Xaa Xaa
    770                 775                 780

Xaa Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa Xaa
        835                 840                 845

Xaa Xaa Xaa Xaa Xaa Xaa Xaa Xaa Xaa Xaa Xaa Xaa Xaa Xaa Xaa Xaa
    850                 855                 860

Xaa Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa Xaa
                885                 890                 895

Xaa Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa Xaa
        915                 920                 925

Xaa Xaa Xaa Xaa Xaa Xaa Xaa Xaa Xaa Xaa Xaa Xaa Xaa Xaa Xaa Xaa
    930                 935                 940

Xaa Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa Xaa
                965                 970                 975

Xaa Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa Xaa Xaa Xaa Xaa Xaa Xaa Xaa Xaa Xaa
        995                 1000                1005

Xaa Xaa Xaa Xaa Xaa Xaa Xaa Xaa Xaa Xaa Xaa Xaa Xaa Xaa Xaa Xaa
    1010                1015                1020
```

```
Xaa Xaa Xaa Xaa Xaa Xaa Xaa Xaa Xaa Xaa Xaa Xaa Xaa Xaa Xaa Xaa
1025                1030                1035                1040

Xaa Xaa Xaa Xaa Xaa Xaa Xaa Xaa Xaa Xaa Xaa Xaa Xaa Xaa Xaa Xaa
                1045                1050                1055

Xaa Xaa Xaa Xaa Xaa Xaa Xaa Xaa Xaa Xaa Xaa Xaa Xaa Xaa Xaa Xaa
            1060                1065                1070

Xaa Xaa Xaa Xaa Xaa Xaa Xaa Xaa Xaa Xaa Xaa Xaa Xaa Xaa Xaa Xaa
        1075                1080                1085

Xaa Xaa Xaa Xaa Xaa Xaa Xaa Xaa Xaa Xaa Xaa Xaa Xaa Xaa Xaa Xaa
    1090                1095                1100

Xaa Xaa Xaa Xaa Xaa Xaa Xaa Xaa Xaa Xaa Xaa Xaa Xaa Xaa Xaa Xaa
1105                1110                1115                1120

Xaa Xaa Xaa Xaa Xaa Xaa Xaa Xaa Xaa Xaa Xaa Xaa Xaa Xaa Xaa Xaa
                1125                1130                1135

Xaa Xaa Xaa Xaa Xaa Xaa Xaa Xaa Xaa Xaa Xaa Xaa Xaa Xaa Xaa Xaa
            1140                1145                1150

Xaa Xaa Xaa Xaa Xaa Xaa Xaa Xaa Xaa Xaa Xaa Xaa Xaa Xaa Xaa Xaa
        1155                1160                1165

Xaa Xaa Xaa Xaa Xaa Xaa Xaa Xaa Xaa Xaa Xaa Xaa Xaa Xaa Xaa Xaa
    1170                1175                1180

Xaa Xaa Xaa Xaa Xaa Xaa Xaa Xaa Xaa Xaa Xaa Xaa Xaa Xaa Xaa Xaa
1185                1190                1195                1200

Xaa Xaa Xaa Xaa Xaa Xaa Xaa Xaa Xaa Xaa Xaa Xaa Xaa Xaa Xaa Xaa
                1205                1210                1215

Xaa Xaa Xaa Xaa Xaa Xaa Xaa Xaa Xaa Xaa Xaa Xaa Xaa Xaa Xaa Xaa
            1220                1225                1230

Xaa Xaa Xaa Xaa Xaa Xaa Xaa Xaa Xaa Xaa Xaa Xaa Xaa Xaa Xaa Xaa
        1235                1240                1245

Xaa Xaa Xaa Xaa Xaa Xaa Xaa Xaa Xaa Xaa Xaa Xaa Xaa Xaa Xaa Xaa
    1250                1255                1260

Xaa Xaa Xaa Xaa Xaa Xaa Xaa Xaa Xaa Xaa Xaa Xaa Xaa Xaa Xaa Xaa
1265                1270                1275                1280

Xaa Xaa Xaa Xaa Xaa Xaa Xaa Xaa Xaa Xaa Xaa Xaa Xaa Xaa Xaa Xaa
                1285                1290                1295

Xaa Xaa Xaa Xaa Xaa Xaa Xaa Xaa Xaa Xaa Xaa Xaa Xaa Xaa Xaa Xaa
            1300                1305                1310

Xaa Xaa Xaa Xaa Xaa Xaa Xaa Xaa Xaa Xaa Xaa Xaa Xaa Xaa Xaa Xaa
        1315                1320                1325

Xaa Xaa Xaa Xaa Xaa Xaa Xaa Xaa Xaa Xaa Xaa Xaa Xaa Xaa Xaa Xaa
    1330                1335                1340

Xaa Xaa Xaa Xaa Xaa Xaa Xaa Xaa Xaa Xaa Xaa Xaa Xaa Xaa Xaa Xaa
1345                1350                1355                1360

Xaa Xaa Xaa Xaa Xaa Xaa Xaa Xaa Xaa Xaa Xaa Xaa Xaa Xaa Xaa Xaa
                1365                1370                1375

Xaa Xaa Xaa Xaa Xaa Xaa Xaa Xaa Xaa Xaa Xaa Xaa Xaa Xaa Xaa Xaa
            1380                1385                1390

Xaa Xaa Xaa Xaa Xaa Xaa Xaa Xaa Xaa Xaa Xaa Xaa Xaa Xaa Xaa Xaa
        1395                1400                1405

Xaa Xaa Xaa Xaa Xaa Xaa Xaa Xaa Xaa Xaa Xaa Xaa Xaa Xaa Xaa Xaa
    1410                1415                1420

Xaa Xaa Xaa Xaa Xaa Xaa Xaa Xaa Xaa Xaa Xaa Xaa Xaa Xaa Xaa Xaa
1425                1430                1435                1440

Xaa Xaa Xaa Xaa Xaa Xaa Xaa Xaa Xaa Xaa Xaa Xaa Xaa Xaa Xaa Xaa
```

```
                1445                1450                1455

Xaa Xaa Xaa Xaa Xaa Xaa Xaa Xaa Xaa Xaa Xaa Xaa Xaa Xaa Xaa Xaa
            1460                1465                1470

Xaa Xaa Xaa Xaa Xaa Xaa Xaa Xaa Xaa Xaa Xaa Xaa Xaa Xaa Xaa Xaa
        1475                1480                1485

Xaa Xaa Xaa Xaa Xaa Xaa Xaa Xaa Xaa Xaa Xaa Xaa Xaa Xaa Xaa Xaa
    1490                1495                1500

Xaa Xaa Xaa Xaa Xaa Xaa Xaa Xaa Xaa Xaa Xaa Xaa Xaa Xaa Xaa Xaa
1505                1510                1515                1520

Xaa Xaa Xaa Xaa Xaa Xaa Xaa Xaa Xaa Xaa Xaa Xaa Xaa Xaa Xaa Xaa
                1525                1530                1535

Xaa Xaa Xaa Xaa Xaa Xaa Xaa Xaa Xaa Xaa Xaa Xaa Xaa Xaa Xaa Xaa
            1540                1545                1550

Xaa Xaa Xaa Xaa Xaa Xaa Xaa Xaa Xaa Xaa Xaa Xaa Xaa Xaa Xaa Xaa
        1555                1560                1565

Xaa Xaa Xaa Xaa Xaa Xaa Xaa Xaa Xaa Xaa Xaa Xaa Xaa Xaa Xaa Xaa
    1570                1575                1580

Xaa Xaa Xaa Xaa Xaa Xaa Xaa Xaa Xaa Xaa Xaa Xaa Xaa Xaa Xaa Xaa
1585                1590                1595                1600

Xaa Xaa Xaa Xaa Xaa Xaa Xaa Xaa Xaa Xaa Xaa Xaa Xaa Xaa Xaa Xaa
                1605                1610                1615

Xaa Xaa Xaa Xaa Xaa Xaa Xaa Xaa Xaa Xaa Xaa Xaa Xaa Xaa Xaa Xaa
            1620                1625                1630

Xaa Xaa Xaa Xaa Xaa Xaa Xaa Xaa Xaa Xaa Xaa Xaa Xaa Xaa Xaa Xaa
        1635                1640                1645

Xaa Xaa Xaa Xaa Xaa Xaa Xaa Xaa Xaa Xaa Xaa Xaa Xaa Xaa Xaa Xaa
    1650                1655                1660

Xaa Xaa Xaa Xaa Xaa Xaa Xaa Xaa Xaa Xaa Xaa Xaa Xaa Xaa Xaa Xaa
1665                1670                1675                1680

Xaa Xaa Xaa Xaa Xaa Xaa Xaa Xaa Xaa Xaa Xaa Xaa Xaa Xaa Xaa Xaa
                1685                1690                1695

Xaa Xaa Xaa Xaa Xaa Xaa Xaa Xaa Xaa Xaa Xaa Xaa Xaa Xaa Xaa Xaa
            1700                1705                1710

Xaa Xaa Xaa Xaa Xaa Xaa Xaa Xaa Xaa Xaa Xaa Xaa Xaa Xaa Xaa Xaa
        1715                1720                1725

Xaa Xaa Xaa Xaa Xaa Xaa Xaa Xaa Xaa Xaa Xaa Xaa Xaa Xaa Xaa Xaa
    1730                1735                1740

Xaa Xaa Xaa Xaa Xaa Xaa Xaa Xaa Xaa Xaa Xaa Xaa Xaa Xaa Xaa Xaa
1745                1750                1755                1760

Xaa Xaa Xaa Xaa Xaa Xaa Xaa Xaa Xaa Xaa Xaa Xaa Xaa Xaa Xaa Xaa
                1765                1770                1775

Xaa Xaa Xaa Xaa Xaa Xaa Xaa Xaa Xaa Xaa Xaa Xaa Xaa Xaa Xaa Xaa
            1780                1785                1790

Xaa Xaa Xaa Xaa Xaa Xaa Xaa Xaa Xaa Xaa Xaa Xaa Xaa Xaa Xaa Xaa
        1795                1800                1805

Xaa Xaa Xaa Xaa Xaa Xaa Xaa Xaa Xaa Xaa Xaa Xaa Xaa Xaa Xaa Xaa
    1810                1815                1820

Xaa Xaa Xaa Xaa Xaa Xaa Xaa Xaa Xaa Xaa Xaa Xaa Xaa Xaa Xaa Xaa
1825                1830                1835                1840

Xaa Xaa Xaa Xaa Xaa Xaa Xaa Xaa Xaa Xaa Xaa Xaa Xaa Xaa Xaa Xaa
                1845                1850                1855

Xaa Xaa Xaa Xaa Xaa Xaa Xaa Xaa Xaa Xaa Xaa Xaa Xaa Xaa Xaa Xaa
            1860                1865                1870
```

```
Xaa Xaa Xaa Xaa Xaa Xaa Xaa Xaa Xaa Xaa Xaa Xaa Xaa Xaa Xaa Xaa
        1875                1880                1885

Xaa Xaa Xaa Xaa Xaa Xaa Xaa Xaa Xaa Xaa Xaa Xaa Xaa Xaa Xaa Xaa
    1890                1895                1900

Xaa Xaa Xaa Xaa Xaa Xaa Xaa Xaa Xaa Xaa Xaa Xaa Xaa Xaa Xaa Xaa
1905                1910                1915                1920

Xaa Xaa Xaa Xaa Xaa Xaa Xaa Xaa Xaa Xaa Xaa Xaa Xaa Xaa Xaa Xaa
                1925                1930                1935

Xaa Xaa Xaa Xaa Xaa Xaa Xaa Xaa Xaa Xaa Xaa Xaa Xaa Xaa Xaa Xaa
            1940                1945                1950

Xaa Xaa Xaa Xaa Xaa Xaa Xaa Xaa Xaa Xaa Xaa Xaa Xaa Xaa Xaa Xaa
        1955                1960                1965

Xaa Xaa Xaa Xaa Xaa Xaa Xaa Xaa Xaa Xaa Xaa Xaa Xaa Xaa Xaa Xaa
    1970                1975                1980

Xaa Xaa Xaa Xaa Xaa Xaa Xaa Xaa Xaa Xaa Xaa Xaa Xaa Xaa Xaa Xaa
1985                1990                1995                2000

Cys Xaa Xaa Xaa Xaa Xaa Xaa Xaa Xaa Xaa Xaa Xaa Xaa Xaa Xaa Xaa
                2005                2010                2015

Xaa Xaa Xaa Xaa Xaa Xaa Xaa Xaa Xaa Xaa Xaa Xaa Xaa Xaa Xaa Xaa
            2020                2025                2030

Xaa Xaa Xaa Xaa Xaa Xaa Xaa Xaa Xaa Xaa Xaa Xaa Xaa Xaa Xaa Xaa
        2035                2040                2045

Xaa Xaa Xaa Cys Xaa Xaa Xaa Xaa Xaa Cys Xaa Xaa Xaa Xaa Xaa Xaa
    2050                2055                2060

Xaa Xaa Xaa Xaa Xaa Xaa Xaa Xaa Xaa Xaa Xaa Xaa Xaa Xaa Xaa Xaa
2065                2070                2075                2080

Xaa Xaa Xaa Xaa Xaa Xaa Xaa Xaa Xaa Xaa Xaa Xaa Xaa Xaa Xaa Xaa
                2085                2090                2095

Xaa Xaa Xaa Xaa Xaa Xaa Xaa Xaa Xaa Xaa Xaa Xaa Xaa Xaa Xaa Xaa
            2100                2105                2110

Xaa Xaa Xaa Xaa Xaa Xaa Xaa Xaa Xaa Xaa Xaa Xaa Xaa Xaa Xaa Xaa
        2115                2120                2125

Xaa Xaa Xaa Xaa Xaa Xaa Xaa Xaa Xaa Xaa Xaa Xaa Xaa Xaa Xaa Xaa
    2130                2135                2140

Xaa Xaa Xaa Xaa Xaa Xaa Xaa Xaa Xaa Xaa Xaa Xaa Xaa Xaa Cys Xaa
2145                2150                2155                2160

Xaa Xaa Xaa Xaa Xaa Xaa Xaa Xaa Xaa Xaa Xaa Xaa Xaa Xaa Xaa Xaa
                2165                2170                2175

Xaa Xaa Xaa Xaa Xaa Xaa Xaa Xaa Xaa Xaa Xaa Xaa Xaa Xaa Xaa Xaa
            2180                2185                2190

Xaa Xaa Xaa Xaa Xaa Xaa Xaa Xaa Xaa Xaa Xaa Xaa Xaa Xaa Xaa Xaa
        2195                2200                2205

Xaa Xaa Xaa Xaa Xaa Xaa Xaa Xaa Xaa Xaa Xaa Xaa Xaa Xaa Xaa Xaa
    2210                2215                2220

Xaa Xaa Xaa Xaa Xaa Xaa Xaa Xaa Xaa Xaa Xaa Xaa Xaa Xaa Xaa Xaa
2225                2230                2235                2240

Xaa Xaa Xaa Xaa Xaa Xaa Xaa Xaa Xaa Xaa Xaa Xaa Xaa Xaa Xaa Xaa
                2245                2250                2255

Xaa Xaa Xaa Cys Xaa Xaa Xaa Xaa Xaa Xaa Xaa Xaa Xaa Xaa Xaa Xaa
            2260                2265                2270

Xaa Xaa Xaa Xaa Xaa Xaa Xaa Xaa Xaa Xaa Xaa Xaa Xaa Xaa Xaa Xaa
        2275                2280                2285

Xaa Xaa Xaa Xaa Xaa Xaa Xaa Xaa Xaa Xaa Xaa Xaa Xaa Xaa Xaa Xaa
    2290                2295                2300
```

```
Xaa Xaa Xaa Xaa Xaa Xaa Cys Xaa Xaa Xaa Xaa Xaa Cys Xaa Xaa Xaa
2305                2310                2315                2320

Xaa Xaa Xaa Xaa Xaa Xaa Xaa Xaa Xaa Xaa Xaa Xaa Xaa Xaa Xaa Xaa
                2325                2330                2335

Xaa Xaa Xaa Xaa Xaa Xaa Xaa Xaa Xaa Xaa Xaa Xaa Xaa Xaa Xaa Xaa
            2340                2345                2350

Xaa Xaa Xaa Xaa Xaa Xaa Xaa Xaa Xaa Xaa Xaa Xaa Xaa Xaa Xaa Cys
        2355                2360                2365

Xaa Xaa Xaa Xaa Xaa Xaa Xaa Xaa Xaa Xaa Xaa Xaa Xaa Xaa Xaa Xaa
    2370                2375                2380

Xaa Xaa Xaa Xaa Xaa Xaa Xaa Xaa Xaa Xaa Xaa Xaa Xaa Xaa Xaa Xaa
2385                2390                2395                2400

Xaa Xaa Xaa Xaa Xaa Xaa Xaa Xaa Xaa Xaa Xaa Xaa Xaa Xaa Xaa Xaa
                2405                2410                2415

Xaa Xaa Xaa Xaa Xaa Xaa Xaa Xaa Xaa Xaa Xaa Xaa Xaa Xaa Xaa Xaa
            2420                2425                2430

Xaa Xaa Xaa Xaa Xaa Xaa Xaa Xaa Xaa Xaa Xaa Xaa Xaa Xaa Xaa Xaa
        2435                2440                2445

Xaa Xaa Xaa Xaa Xaa Xaa Xaa Xaa Xaa Xaa Xaa Xaa Xaa Xaa Xaa Xaa
    2450                2455                2460

Xaa Xaa Xaa Xaa Xaa Xaa Xaa Xaa Xaa Xaa Xaa Xaa Xaa Xaa Xaa Xaa
2465                2470                2475                2480

Xaa Xaa Xaa Xaa Xaa Xaa Xaa Xaa Xaa Xaa Xaa Xaa Xaa Xaa Xaa Xaa
                2485                2490                2495

Xaa Xaa Xaa Xaa Xaa Xaa Xaa Xaa Xaa Xaa Xaa Xaa Xaa Xaa Xaa Xaa
            2500                2505                2510

Xaa Xaa Xaa Xaa Xaa Xaa Xaa Xaa Xaa Xaa Xaa Xaa Xaa Xaa Xaa Xaa
        2515                2520                2525

Xaa Xaa Xaa Xaa Xaa Xaa Xaa Xaa Xaa Xaa Xaa Xaa Xaa Xaa Xaa Xaa
    2530                2535                2540

Xaa Xaa Xaa Xaa Xaa Xaa Xaa Xaa Xaa Xaa Xaa Xaa Xaa Xaa Xaa Xaa
2545                2550                2555                2560

Xaa Xaa Xaa Xaa Xaa Xaa Xaa Xaa Xaa Xaa Xaa Xaa Xaa Xaa Xaa Xaa
                2565                2570                2575

Xaa Xaa Xaa Xaa Xaa Xaa Xaa Xaa Xaa Xaa Xaa Xaa Xaa Xaa Xaa Xaa
            2580                2585                2590

Xaa Xaa Xaa Xaa Xaa Xaa Xaa Xaa Xaa Xaa Xaa Xaa Xaa Xaa Xaa Xaa
        2595                2600                2605

Xaa Xaa Xaa Xaa Xaa Xaa Xaa Xaa Xaa Xaa Xaa Xaa Xaa Xaa Xaa Xaa
    2610                2615                2620

Xaa Xaa Xaa Xaa Xaa Xaa Xaa Xaa Xaa Xaa Xaa Xaa Xaa Xaa Xaa Xaa
2625                2630                2635                2640

Xaa Xaa Xaa Xaa Xaa Xaa Xaa Xaa Xaa Xaa Xaa Xaa Xaa Xaa Xaa Xaa
                2645                2650                2655

Xaa Xaa Xaa Xaa Xaa Xaa Xaa Xaa Xaa Xaa Xaa Xaa Xaa Xaa Xaa Xaa
            2660                2665                2670

Xaa Xaa Xaa Xaa Xaa Xaa Xaa Xaa Xaa Xaa Xaa Xaa Xaa Xaa Xaa Xaa
        2675                2680                2685

Xaa Xaa Xaa Xaa Xaa Xaa Xaa Xaa Xaa Xaa Xaa Xaa Xaa Xaa Xaa Xaa
    2690                2695                2700

Xaa Xaa Xaa Xaa Xaa Xaa Xaa Xaa Xaa Xaa Xaa Xaa Xaa Xaa Xaa Xaa
2705                2710                2715                2720

Xaa Xaa Xaa Xaa Xaa Xaa Xaa Xaa Xaa Xaa Xaa Xaa Xaa Xaa Xaa Xaa
```

```
                2725                2730                2735

Xaa Xaa Xaa Xaa Xaa Xaa Xaa Xaa Xaa Xaa Xaa Xaa Xaa Xaa Xaa Xaa
            2740                2745                2750

Xaa Xaa Xaa Xaa Xaa Xaa Xaa Xaa Xaa Xaa Xaa Xaa Xaa Xaa Xaa Xaa
        2755                2760                2765

Xaa Xaa Xaa Xaa Xaa Xaa Xaa Xaa Xaa Xaa Xaa Xaa Xaa Xaa Xaa Xaa
    2770                2775                2780

Xaa Xaa Xaa Xaa Xaa Xaa Xaa Xaa Xaa Xaa Xaa Xaa Xaa Xaa Xaa Xaa
2785                2790                2795                2800

Xaa Xaa Xaa Xaa Xaa Xaa Xaa Xaa Xaa Xaa Xaa Xaa Xaa Xaa Xaa Xaa
                2805                2810                2815

Xaa Xaa Xaa Xaa Xaa Xaa Xaa Xaa Xaa Xaa Xaa Xaa Xaa Xaa Xaa Xaa
            2820                2825                2830

Xaa Xaa Xaa Xaa Xaa Xaa Xaa Xaa Xaa Xaa Xaa Xaa Xaa Xaa Xaa Xaa
        2835                2840                2845

Xaa Xaa Xaa Xaa Xaa Xaa Xaa Xaa Xaa Xaa Xaa Xaa Xaa Xaa Xaa Xaa
    2850                2855                2860

Xaa Xaa Xaa Xaa Xaa Xaa Xaa Xaa Xaa Xaa Xaa Xaa Xaa Xaa Xaa Xaa
2865                2870                2875                2880

Xaa Xaa Xaa Xaa Xaa Xaa Xaa Xaa Xaa Xaa Xaa Xaa Xaa Xaa Xaa Xaa
                2885                2890                2895

Xaa Xaa Xaa Xaa Xaa Xaa Xaa Xaa Xaa Xaa Xaa Xaa Xaa Xaa Xaa Xaa
            2900                2905                2910

Xaa Xaa Xaa Xaa Xaa Xaa Xaa Xaa Xaa Xaa Xaa Xaa Xaa Xaa Xaa Xaa
        2915                2920                2925

Xaa Xaa Xaa Xaa Xaa Xaa Xaa Xaa Xaa Xaa Xaa Xaa Xaa Xaa Xaa Xaa
    2930                2935                2940

Xaa Xaa Xaa Xaa Xaa Xaa Xaa Xaa Xaa Xaa Xaa Xaa Xaa Xaa Xaa Xaa
2945                2950                2955                2960

Xaa Xaa Xaa Xaa Xaa Xaa Xaa Xaa Xaa Xaa Xaa Xaa Xaa Xaa Xaa Xaa
                2965                2970                2975

Xaa Xaa Xaa Xaa Xaa Xaa Xaa Xaa Xaa Xaa Xaa Xaa Xaa Xaa Xaa Xaa
            2980                2985                2990

Xaa Xaa Xaa Xaa Xaa Xaa Xaa Xaa Xaa Xaa Xaa Xaa Xaa Xaa Xaa Xaa
        2995                3000                3005

Xaa Xaa Xaa Xaa Xaa Xaa Xaa Xaa Xaa Xaa Xaa Xaa Xaa Xaa Xaa Xaa
    3010                3015                3020

Xaa Xaa Xaa Xaa Xaa Xaa Xaa Xaa Xaa Xaa Xaa Xaa Xaa Xaa Xaa Xaa
3025                3030                3035                3040

Xaa Xaa Xaa Xaa Xaa Xaa Xaa Xaa Xaa Xaa Xaa Xaa Xaa Xaa Xaa Xaa
                3045                3050                3055

Xaa Xaa Xaa Xaa Xaa Xaa Xaa Xaa Xaa Xaa Xaa Xaa Xaa Xaa Xaa Xaa
            3060                3065                3070

Xaa Xaa Xaa Xaa Xaa Xaa Xaa Xaa Xaa Xaa Xaa Xaa Xaa Xaa Xaa Xaa
        3075                3080                3085

Xaa Xaa Xaa Xaa Xaa Xaa Xaa Xaa Xaa Xaa Xaa Xaa Xaa Xaa Xaa Xaa
    3090                3095                3100

Xaa Xaa Xaa Xaa Xaa Xaa Xaa Xaa Xaa Xaa Xaa Xaa Xaa Xaa Xaa Xaa
3105                3110                3115                3120

Xaa Xaa Xaa Xaa Xaa Xaa Xaa Xaa Xaa Xaa Xaa Xaa Xaa Xaa Xaa Xaa
                3125                3130                3135

Xaa Xaa Xaa Xaa Xaa Xaa Xaa Xaa Xaa Xaa Xaa Xaa Xaa Xaa Xaa Xaa
            3140                3145                3150
```

```
Xaa Xaa Xaa Xaa Xaa Xaa Xaa Xaa Xaa Xaa Xaa Xaa Xaa Xaa Xaa Xaa
        3155                3160                3165

Xaa Xaa Xaa Xaa Xaa Xaa Xaa Xaa Xaa Xaa Xaa Xaa Xaa Xaa Xaa Xaa
    3170                3175                3180

Xaa Xaa Xaa Xaa Xaa Xaa Xaa Xaa Xaa Xaa Xaa Xaa Xaa Xaa Xaa Xaa
3185                3190                3195                3200

Xaa Xaa Xaa Xaa Xaa Xaa Xaa Xaa Xaa Xaa Xaa Xaa Xaa Xaa Xaa Xaa
                3205                3210                3215

Xaa Xaa Xaa Xaa Xaa Xaa Xaa Xaa Xaa Xaa Xaa Xaa Xaa Xaa Xaa Xaa
            3220                3225                3230

Xaa Xaa Xaa Xaa Xaa Xaa Xaa Xaa Xaa Xaa Xaa Xaa Xaa Xaa Xaa Xaa
        3235                3240                3245

Xaa Xaa Xaa Xaa Xaa Xaa Xaa Xaa Xaa Xaa Xaa Xaa Xaa Xaa Xaa Xaa
    3250                3255                3260

Xaa Xaa Xaa Xaa Xaa Xaa Xaa Xaa Xaa Xaa Xaa Xaa Xaa Xaa Xaa Xaa
3265                3270                3275                3280

Xaa Xaa Xaa Xaa Xaa Xaa Xaa Xaa Xaa Xaa Xaa Xaa Xaa Xaa Xaa Xaa
                3285                3290                3295

Xaa Xaa Xaa Xaa Xaa Xaa Xaa Xaa Xaa Xaa Xaa Xaa Xaa Xaa Xaa Xaa
            3300                3305                3310

Xaa Xaa Xaa Xaa Xaa Xaa Xaa Xaa Xaa Xaa Xaa Xaa Xaa Xaa Xaa Xaa
        3315                3320                3325

Xaa Xaa Xaa Xaa Xaa Xaa Xaa Xaa Xaa Xaa Xaa Xaa Xaa Xaa Xaa Xaa
    3330                3335                3340

Xaa Xaa Xaa Xaa Xaa Xaa Xaa Xaa Xaa Xaa Xaa Xaa Xaa Xaa Xaa Xaa
3345                3350                3355                3360

Xaa Xaa Xaa Xaa Xaa Xaa Xaa Xaa Xaa Xaa Xaa Xaa Xaa Xaa Xaa Xaa
                3365                3370                3375

Xaa Xaa Xaa Xaa Xaa Xaa Xaa Xaa Xaa Xaa Xaa Xaa Xaa Xaa Xaa Xaa
            3380                3385                3390

Xaa Xaa Xaa Xaa Xaa Xaa Xaa Xaa Xaa Xaa Xaa Xaa Xaa Xaa Xaa Xaa
        3395                3400                3405

Xaa Xaa Xaa Xaa Xaa Xaa Xaa Xaa Xaa Xaa Xaa Xaa Xaa Xaa Xaa Xaa
    3410                3415                3420

Xaa Xaa Xaa Xaa Xaa Xaa Xaa Xaa Xaa Xaa Xaa Xaa Xaa Xaa Xaa Xaa
3425                3430                3435                3440

Xaa Xaa Xaa Xaa Xaa Xaa Xaa Xaa Xaa Xaa Xaa Xaa Xaa Xaa Xaa Xaa
                3445                3450                3455

Xaa Xaa Xaa Xaa Xaa Xaa Xaa Xaa Xaa Xaa Xaa Xaa Xaa Xaa Xaa Xaa
            3460                3465                3470

Xaa Xaa Xaa Xaa Xaa Xaa Xaa Xaa Xaa Xaa Xaa Xaa Xaa Xaa Xaa Xaa
        3475                3480                3485

Xaa Xaa Xaa Xaa Xaa Xaa Xaa Xaa Xaa Xaa Xaa Xaa Xaa Xaa Xaa Xaa
    3490                3495                3500

Xaa Xaa Xaa Xaa Xaa Xaa Xaa Xaa Xaa Xaa Xaa Xaa Xaa Xaa Xaa Xaa
3505                3510                3515                3520

Xaa Xaa Xaa Xaa Xaa Xaa Xaa Xaa Xaa Xaa Xaa Xaa Xaa Xaa Xaa Xaa
                3525                3530                3535

Xaa Xaa Xaa Xaa Xaa Xaa Xaa Xaa Xaa Xaa Xaa Xaa Xaa Xaa Xaa Xaa
            3540                3545                3550

Xaa Xaa Xaa Xaa Xaa Xaa Xaa Xaa Xaa Xaa Xaa Xaa Xaa Xaa Xaa Xaa
        3555                3560                3565

Xaa Xaa Xaa Xaa Xaa Xaa Xaa Xaa Xaa Xaa Xaa Xaa Xaa Xaa Xaa Xaa
    3570                3575                3580
```

```
Xaa Xaa Xaa Xaa Xaa Xaa Xaa Xaa Xaa Xaa Xaa Xaa Xaa Xaa Xaa Xaa
3585                3590                3595                3600

Xaa Xaa Xaa Xaa Xaa Xaa Xaa Xaa Xaa Xaa Xaa Xaa Xaa Xaa Xaa Xaa
                3605                3610                3615

Xaa Xaa Xaa Xaa Xaa Xaa Xaa Xaa Xaa Xaa Xaa Xaa Xaa Xaa Xaa Xaa
            3620                3625                3630

Xaa Xaa Xaa Xaa Xaa Xaa Xaa Xaa Xaa Xaa Xaa Xaa Xaa Xaa Xaa Xaa
        3635                3640                3645

Xaa Xaa Xaa Xaa Xaa Xaa Xaa Xaa Xaa Xaa Xaa Xaa Xaa Xaa Xaa Xaa
    3650                3655                3660

Xaa Xaa Xaa Xaa Xaa Xaa Xaa Xaa Xaa Xaa Xaa Xaa Xaa Xaa Xaa Xaa
3665                3670                3675                3680

Xaa Xaa Xaa Xaa Xaa Xaa Xaa Xaa Xaa Xaa Xaa Xaa Xaa Xaa Xaa Xaa
                3685                3690                3695

Xaa Xaa Xaa Xaa Xaa Xaa Xaa Xaa Xaa Xaa Xaa Xaa Xaa Xaa Xaa Xaa
            3700                3705                3710

Xaa Xaa Xaa Xaa Xaa Xaa Xaa Xaa Xaa Xaa Xaa Xaa Xaa Xaa Xaa Xaa
        3715                3720                3725

Xaa Xaa Xaa Xaa Xaa Xaa Xaa Xaa Xaa Xaa Xaa Xaa Xaa Xaa Xaa Xaa
    3730                3735                3740

Xaa Xaa Xaa Xaa Xaa Xaa Xaa Xaa Xaa Xaa Xaa Xaa Xaa Xaa Xaa Xaa
3745                3750                3755                3760

Xaa Xaa Xaa Xaa Xaa Xaa Xaa Xaa Xaa Xaa Xaa Xaa Xaa Xaa Xaa Xaa
                3765                3770                3775

Xaa Xaa Xaa Xaa Xaa Xaa Xaa Xaa Xaa Xaa Xaa Xaa Xaa Xaa Xaa Xaa
            3780                3785                3790

Xaa Xaa Xaa Xaa Xaa Xaa Xaa Xaa Xaa Xaa Xaa Xaa Xaa Xaa Xaa Xaa
        3795                3800                3805

Xaa Xaa Xaa Xaa Xaa Xaa Xaa Xaa Xaa Xaa Xaa Xaa Xaa Xaa Xaa Xaa
    3810                3815                3820

Xaa Xaa Xaa Xaa Xaa Xaa Xaa Xaa Xaa Xaa Xaa Xaa Xaa Xaa Xaa Xaa
3825                3830                3835                3840

Xaa Xaa Xaa Xaa Xaa Xaa Xaa Xaa Xaa Xaa Xaa Xaa Xaa Xaa Xaa Xaa
                3845                3850                3855

Xaa Xaa Xaa Xaa Xaa Xaa Xaa Xaa Xaa Xaa Xaa Xaa Xaa Xaa Xaa Xaa
            3860                3865                3870

Xaa Xaa Xaa Xaa Xaa Xaa Xaa Xaa Xaa Xaa Xaa Xaa Xaa Xaa Xaa Xaa
        3875                3880                3885

Xaa Xaa Xaa Xaa Xaa Xaa Xaa Xaa Xaa Xaa Xaa Xaa Xaa Xaa Xaa Xaa
    3890                3895                3900

Xaa Xaa Xaa Xaa Xaa Xaa Xaa Xaa Xaa Xaa Xaa Xaa Xaa Xaa Xaa Xaa
3905                3910                3915                3920

Xaa Xaa Xaa Xaa Xaa Xaa Xaa Xaa Xaa Xaa Xaa Xaa Xaa Xaa Xaa Xaa
                3925                3930                3935

Xaa Xaa Xaa Xaa Xaa Xaa Xaa Xaa Xaa Xaa Xaa Xaa Xaa Xaa Xaa Xaa
            3940                3945                3950

Xaa Xaa Xaa Xaa Xaa Xaa Xaa Xaa Xaa Xaa Xaa Xaa Xaa Xaa Xaa Xaa
        3955                3960                3965

Xaa Xaa Xaa Xaa Xaa Xaa Xaa Xaa Xaa Xaa Xaa Xaa Xaa Xaa Xaa Xaa
    3970                3975                3980

Xaa Xaa Xaa Xaa Xaa Xaa Xaa Xaa Xaa Xaa Xaa Xaa Xaa Xaa Xaa Xaa
3985                3990                3995                4000

Xaa Xaa Xaa Xaa Xaa Xaa Xaa Xaa Xaa Xaa Xaa Xaa Xaa Xaa Xaa Xaa
```

-continued

```
                4005                4010                4015

Xaa Xaa Xaa Xaa Xaa Xaa Xaa Xaa Xaa Xaa Xaa Xaa Xaa Xaa Xaa Xaa
            4020                4025                4030

Xaa Xaa Xaa Xaa Xaa Xaa Xaa Xaa Xaa Xaa Xaa Xaa Xaa Xaa Xaa Xaa
        4035                4040                4045

Xaa Xaa Xaa Xaa Xaa Xaa Xaa Xaa Xaa Xaa Xaa Xaa Xaa Xaa Xaa Xaa
    4050                4055                4060

Xaa Xaa Xaa Xaa Xaa Xaa Xaa Xaa Xaa Xaa Xaa Xaa Xaa Xaa Xaa Xaa
4065                4070                4075                4080

Xaa Xaa Xaa Xaa Xaa Xaa Xaa Xaa Xaa Xaa Xaa Xaa Xaa Xaa Xaa Xaa
                4085                4090                4095

Xaa Xaa Xaa Xaa Xaa Xaa Xaa Xaa Xaa Xaa Xaa Xaa Xaa Xaa Xaa Xaa
            4100                4105                4110

Xaa Xaa Xaa Xaa Xaa Xaa Xaa Xaa Xaa Xaa Xaa Xaa Xaa Xaa Xaa Xaa
        4115                4120                4125

Xaa Xaa Xaa Xaa Xaa Xaa Xaa Xaa Xaa Xaa Xaa Xaa Xaa Xaa Xaa Xaa
    4130                4135                4140

Xaa Xaa Xaa Xaa Xaa Xaa Xaa Xaa Xaa Xaa Xaa Xaa Xaa Xaa Xaa Xaa
4145                4150                4155                4160

Xaa Xaa Xaa Xaa Xaa Xaa Xaa Xaa Xaa Xaa Xaa Xaa Xaa Xaa Xaa Xaa
                4165                4170                4175

Xaa Xaa Xaa Xaa Xaa Xaa Xaa Xaa Xaa Xaa Xaa Xaa Xaa Xaa Xaa Xaa
            4180                4185                4190

Xaa Xaa Xaa Xaa Xaa Xaa Xaa Xaa Xaa Xaa Xaa Xaa Xaa Xaa Xaa Xaa
        4195                4200                4205

Xaa Xaa Xaa Xaa Xaa Xaa Xaa Xaa Xaa Xaa Xaa Xaa Xaa Xaa Xaa Xaa
    4210                4215                4220

Xaa Xaa Xaa Xaa Xaa Xaa Xaa Xaa Xaa Xaa Xaa Xaa Xaa Xaa Xaa Xaa
4225                4230                4235                4240

Xaa Xaa Xaa Xaa Xaa Xaa Xaa Xaa Xaa Xaa Xaa Xaa Xaa Xaa Xaa Xaa
                4245                4250                4255

Xaa Xaa Xaa Xaa Xaa Xaa Xaa Xaa Xaa Xaa Xaa Xaa Xaa Xaa Xaa Xaa
            4260                4265                4270

Xaa Xaa Xaa Xaa Xaa Xaa Xaa Xaa Xaa Xaa Xaa Xaa Xaa Xaa Xaa Xaa
        4275                4280                4285

Xaa Xaa Xaa Xaa Xaa Xaa Xaa Xaa Xaa Xaa Xaa Xaa Xaa Xaa Xaa Xaa
    4290                4295                4300

Xaa Xaa Xaa Xaa Xaa Xaa Xaa Xaa Xaa Xaa Xaa Xaa Xaa Xaa Xaa Xaa
4305                4310                4315                4320

Xaa Xaa Xaa Xaa Xaa Xaa Xaa Xaa Xaa Xaa Xaa Xaa Xaa Xaa Xaa Xaa
                4325                4330                4335

Xaa Xaa Xaa Xaa Xaa Xaa Xaa Xaa Xaa Xaa Xaa Xaa Xaa Xaa Xaa Xaa
            4340                4345                4350

Xaa Xaa Xaa Xaa Xaa Xaa Xaa Xaa Xaa Xaa Xaa Xaa Xaa Xaa Xaa Xaa
        4355                4360                4365
```

The invention claimed is:

1. Process for extracting hydrophobin from a solution comprising the steps of:

a) adding carrageenan to the solution;

b) adjusting the pH of the solution to below 3.5;

c) filtering the solution to produce a retentate and a filtrate; *and* d) recovering the hydrophobin from the retentate;

[e) centrifuging the solution to produce a supernatant which is removed, leaving a remaining phase; and f) removing the hydrophobin from the remaining phase;]

wherein the resulting hydrophobin is suitable for use in foods, personal care products and medicine.

2. Process according to claim 1 further comprising the step of cultivating a host cell in the solution including a fermentation medium wherein the host cell extra-cellularly secretes hydrophobin; and the fermentation medium contains an antifoam.

3. Process according to claim 2 wherein the host cell is a genetically-modified fungus.

4. Process according to claim 3 wherein the host cell is a yeast.

5. Process according to claim 4 wherein the host cell is Saccharomyces cerevisiae.

6. Process according to claim 1 wherein the hydrophobin is HFBI or HFBII from Trichoderma reesei.

7. Process according to claim 1 wherein the solution has an ionic strength below 0.5.

8. Process according to claim 1 wherein the carrageenan is kappa or iota carrageenan.

9. Process according to claim 8 wherein the carrageenan is iota carrageenan.

10. Process according to claim 1 wherein the carrageenan/hydrophobin ratio (w/w) is between 1:10 and 10:1.

11. Process according to claim 1 wherein the carrageenan is a shear gel.

*12. Process for extracting hydrophobin from a solution comprising the steps of:*

*a) adding carrageenan to the solution;*

*b) adjusting the pH of the solution to below 3.5;*

*c) centrifuging the solution to produce a supernatant which is removed, leaving a remaining phase; and*

*d) removing the hydrophobin from the remaining phase; wherein the resulting hydrophobin is suitable for use in foods, personal care products and medicine.*

*13. Process according to claim 12 further comprising the step of cultivating a host cell in the solution including a fermentation medium wherein the host cell extra-cellularly secretes hydrophobin; and the fermentation medium contains an antifoam.*

*14. Process according to claim 13 wherein the host cell is a genetically-modified fungus.*

*15. Process according to claim 14 wherein the host cell is a yeast.*

*16. Process according to claim 15 wherein the host cell is Saccharomyces cerevisiae.*

*17. Process according to claim 12 wherein the hydrophobin is HFBI or HFBII from Trichoderma reesei.*

*18. Process according to claim 12 wherein the solution has an ionic strength below 0.5.*

*19. Process according to claim 12 wherein the carrageenan is kappa or iota carrageenan.*

*20. Process according to claim 19 wherein the carrageenan is iota carrageenan.*

*21. Process according to claim 12 wherein the carrageenan/hydrophobin ratio (w/w) is between 1:10 and 10:1.*

*22. Process according to claim 12 wherein the carrageenan is a shear gel.*

* * * * *